(12) United States Patent
Salceda et al.

(10) Patent No.: US 6,902,892 B1
(45) Date of Patent: Jun. 7, 2005

(54) METHOD OF DIAGNOSING, MONITORING, STAGING, IMAGING AND TREATING PROSTATE CANCER

(75) Inventors: Susan Salceda, San Jose, CA (US); Herve Recipon, San Francisco, CA (US); Robert Cafferkey, South San Francisco, CA (US)

(73) Assignee: diaDexus, Inc., South San Francisco, CA (US)

(*) Notice: Subject to any disclaimer, the term of this patent is extended or adjusted under 35 U.S.C. 154(b) by 0 days.

(21) Appl. No.: 09/807,201

(22) PCT Filed: Oct. 19, 1999

(86) PCT No.: PCT/US99/24331

§ 371 (c)(1),
(2), (4) Date: Apr. 25, 2001

(87) PCT Pub. No.: WO00/23111

PCT Pub. Date: Apr. 27, 2000

Related U.S. Application Data

(60) Provisional application No. 60/104,737, filed on Oct. 19, 1998.

(51) Int. Cl.[7] ................................................ C12Q 1/68
(52) U.S. Cl. ..................... 435/6; 435/91.2; 536/23.1; 536/23.5; 536/24.3
(58) Field of Search ............................... 435/6; 536/23.1

(56) References Cited

U.S. PATENT DOCUMENTS

| | | | |
|---|---|---|---|
| 5,514,579 A | 5/1996 | O'Hara et al. | |
| 5,912,143 A | * 6/1999 | Bandman et al. | .......... 435/69.1 |
| 5,952,011 A | 9/1999 | O'Hara et al. | |
| 6,043,033 A | 3/2000 | Bandman et al. | |
| 6,203,979 B1 | 3/2001 | Bandman et al. | |
| 6,262,245 B1 | 7/2001 | Xu et al. | |
| 6,294,663 B1 | 9/2001 | O'Brien et al. | |
| 6,350,448 B1 | 2/2002 | Bandman et al. | |

FOREIGN PATENT DOCUMENTS

| | | |
|---|---|---|
| EP | 1033401 A2 | 9/2000 |
| JP | 11032768 A2 | 2/1999 |
| WO | WO 93/13207 A2 | 7/1993 |
| WO | WO 98/20165 A2 | 5/1998 |
| WO | WO 98/36054 A1 | 8/1998 |
| WO | WO 98/37093 A2 | 8/1998 |
| WO | WO 98/37418 A2 | 8/1998 |
| WO | WO 98/45435 A2 | 10/1998 |
| WO | WO 99/06548 A2 | 2/1999 |
| WO | WO 99/14328 A2 | 3/1999 |
| WO | WO 99/36550 A2 | 7/1999 |
| WO | WO 99/37811 A1 | 7/1999 |
| WO | WO 99/57132 A1 | 11/1999 |
| WO | WO 99/60162 A1 | 11/1999 |
| WO | WO 99/62941 A2 | 12/1999 |
| WO | WO 99/62942 A2 | 12/1999 |
| WO | WO 99/67384 | 12/1999 |
| WO | WO 00/00605 A1 | 1/2000 |
| WO | WO 00/04149 A2 | 1/2000 |
| WO | WO 00/12706 A1 | 3/2000 |
| WO | WO 00/12758 A1 | 3/2000 |
| WO | WO 00/14234 A1 | 3/2000 |
| WO | WO 00/16805 A1 | 3/2000 |
| WO | WO 00/18961 A2 | 4/2000 |
| WO | WO 00/23111 A1 | 4/2000 |
| WO | WO 00/29448 A2 | 5/2000 |
| WO | WO 00/36107 A2 | 6/2000 |
| WO | WO 00/43495 A2 | 7/2000 |
| WO | WO 00/55351 A1 | 9/2000 |
| WO | WO 00/55629 A2 | 9/2000 |
| WO | WO 00/73454 A1 | 12/2000 |
| WO | WO 00/76531 A1 | 12/2000 |
| WO | WO 00/78960 A2 | 12/2000 |
| WO | WO 01/04311 A1 | 1/2001 |
| WO | WO 01/16289 A2 | 3/2001 |
| WO | WO 01/23547 A1 | 4/2001 |
| WO | WO 01/25272 A2 | 4/2001 |
| WO | WO 01/27257 A1 | 4/2001 |
| WO | WO 01/34802 A2 | 5/2001 |
| WO | WO 01/51633 A2 | 7/2001 |

OTHER PUBLICATIONS

Kibel, AS et al, 2000, J urol, 164(1): 192–6.*
Ren, C et al, 1998, Cancer Res, 58(6): 1285–90.*
Gingrich, JR et al, 1996, Cancer res, 56(18): 4096–4102.*
Jacquinet E et al, 2001, Eur J Biochem, 268 (9): 2687–2699, and MPSRCH sequence similarity search report, 2003, us–09–807–201–8.rge, pp. 7–8.*
Harris et al. J. of The Am Society of Nephrology 6:1125–33, 1995.*
;Ahn et al. Nature Genetics 3(4):283–91, 1993.*
Cawthon et al. Genomics 9(3):446–60, 1991.*
van de Vijver, M et al, 1987, Mol Cell Biol, 7(5): 2019–2023.*
Afar et al., "Catalytic Cleavage of the Androgen–regulated TMPRSS2 Protease Results in Its Secretion by Prostate and Prostate Cancer Epithelia", Cancer Research 2001 61:1686–1692 XP–002229964.
Lin et al., "Prostate–localized and Androgen–regulated Expression of the Membrane–bound Serine Protease TMPRSS2[1]", Cancer Research 1999 59:4180–4184 XP–000929801.
Jacquinet et al., "*Homo sapiens* epitheliasin (TMPRSS2) mRNA, complete cds." 2001 Accession No. AF329454 XP–002229966.
Paoloni–Giacobino et al., "Homo serine protease mRNA, complete cds." 1997 Accession No. U75329 XP–002229965.
Blok et al., "Isolation of cDNAs That Are Differentially Expressed Between Androgen–Dependent and Androgen–Independent Prostate Carcinoma Cells Using Differentially Disply PCR", The Prostate 1995 26:213–224.

(Continued)

*Primary Examiner*—Susan Ungar
*Assistant Examiner*—Minh Tam Davis
(74) *Attorney, Agent, or Firm*—Licata & Tyrrell P.C.; Nathan P. Letts

(57) ABSTRACT

The present invention provides new methods for detecting, diagnosing, monitoring, staging, prognosticating, imaging and treating prostate cancer.

9 Claims, No Drawings

OTHER PUBLICATIONS

Chang et al., "Differentially Expressed Genes in Androgen-dependent and –independent Prostate Carcinomas[1]", Cancer Research 1997 57:4075–4081.

Friedrich et al., "Differention–Stage Specific Expression of Oncoprotein 18 in Human and Rat Prostatic Andeocarcinoma", The Prostate 1995 27:102–109.

Gagnon et al., "Expression of Zn–Alpha$^2$–Glycoprotein and PSP–94 in Prostatic Adenocarcinoma", American Journal of Pathology 1990 136(5):1147–1152.

Hale et al., "Zinc α–2–Glycoprotein Is Expressed by Malignant Prostatic Epithelium and May Serve as a Potential Serum Marker for Prostate Cancer[1]", Clinical Cancer Research 2001 7(7):846–853.

López–Otín et al., "Breast and Prostate Cancer:An Analysis of Common Epidemiological, Genetic and Biochemical Features", Endocrine Reviews 1998 19(4):365–396.

Olsson et al., "Reverse Transcriptase–Polymerase Chain Reaction Assays for Prostate Cancer", Urologic Clinics of North America 1997 24 (2):367–378.

Ueyama et al., "Molecular Cloning and Chromosomal Assignment of the Gene for Human Zn–$\alpha_2$–glycoportein", Biochemistry 1993 32:12968–12976.

EMB/GenBank/DDBJ XO–002220465 –Ueyama et al., "Molecular Cloning and Chromosomal Assignment of the Gene for Human Zn–$\alpha_2$–glycoportein", Biochemistry 1993 32:12968–12976.

Paoloni–Giacobino et al. Cloning of the TMPRSS2 gene, which encodes a novel serine protease with transmembrane, LDLRA, and SRCR domains and maps to 21q22.3, Genomics, 1997; 44:309–320.

Pasquali et al. Changes in tissue transglutaminase activity and expression during retinoic acid–induced growth arrest and apoptosis in primary cultures of human epithelial prostate cells. J Clin Endocin & Metab. 1999;84(4):1463–1469.

Brinkmann et al. *PAGE–1*, an X chromosome–linked *GAGE*–like gene that is expressed in normal and neoplastic prostate, testis, and uterus. PNAS. Sept 1998;95:10757–10762.

Chen et al. Isolation and characterization of *PAGE–1* and *GAGE–7*. JBC. Jul. 10, 1998;273(28):17618–17625.

Dannull et al. Prostate stem cell antigen is a promising candidate for immunotherapy of advanced prostate cancer. Can. Res. Oct. 1, 2000;60(19):5323–5598.

An G, Meka CS, Bright SP, Veltri RW. Human prostate–specific transglutaminase gene: promoter cloning, tissue–specific expression, and down–regulation in metastatic prostate cancer. Urology. Dec. 1999;54(6):1105–11.

Dubbink HJ, Cleutjens KB, van der Korput HA, Trapman J, Romijn JC. An Sp1 binding site is essential for basal activity of the human prostate–specific transglutaminase gene (TGM4) promoter. Gene. Nov. 29, 1999, vol. 240(2), pp. 261–267.

Dubbink HJ, Hoedemaeker RF, van der Kwast TH, Schroder FH, Romijn JC. Human prostate–specific transglutaminase: a new prostatic marker with a unique distribution pattern. Lab Invest. Feb. 1999, vol. 79(2), pp. 141–150.

Dubbink,H.J., de Waal,L., van Haperen,R., Verkaik,N.S., Trapman,J. and Romijn,J.C. The human prostate–specific transglutaminase gene (TGM4): genomic organization, tissue–specific expression, and promoter characterization. Genomics, vol. 51(3), 1998, pp. 434–444.

Dubbink,H.J., Verkaik,N.S., Faber,P.W., Trapman,J., Schroder,F.H. and Romijn,J.C. Tissue specific and androgen––regulated expression of human prostate–specific transglutaminase. Biochem. J. vol. 315(Pt3), 1996, pp. 901–908.

Gentile V, Grant FJ, Porta R and Baldini A. Localization of the human prostate transglutaminase (type IV) gene. (TGM4) to chromosome 3p21.33–p22 by fluorescence in situ hybridization. Genomics, vol. 27(1), 1995, pp. 219–220.

Goebel HW, Rausch U, Steinhoff M, Seitz J, Bacher M, Papotti M, Bussolati G, Tuohimaa P, Aumuller G. Arguments against the prostatic origin of the R–3327 Dunning H tumor. Virchows Arch B Cell Pathol Incl Mol Pathol. 1992, vol. 62(1), pp. 9–18.

Grant FJ, Taylor DA, Sheppard PO, Mathewes SL, Lint W, Vanaja E, Bishop PD and O'Hara PJ. Molecular cloning and characterization of a novel transglutaminase cDNA from a human prostate cDNA library, Biochem. Biophys. Res. Commun. vol. 203(2), 1994, pp. 1117–1123.

Bussemakers et al., "DD3:A New Prostate–specific Gene, Highly Overexpressed in Prostate Cancer[1]", Cancer Research 1999 59(23):5975–5979.

Cho–Chung Y.S., "Antisense oligonucleotides for the treatment of cancer", Curr. Opin. Thera. Patents 1993 3(12):1737–1750.

Olsson et al., "Reverse Transcriptase–Polymerase Chain Reaction Assays for Prostate Cancer", Urologic Clinics of North America 1997 24(2):367–378.

* cited by examiner

METHOD OF DIAGNOSING, MONITORING, STAGING, IMAGING AND TREATING PROSTATE CANCER

This application claims the benefit of No. 60/104,737 filed Oct. 19, 1998.

FIELD OF THE INVENTION

This invention relates, in part, to newly developed assays for detecting, diagnosing, monitoring, staging, prognosticating, imaging and treating cancers, particularly prostate cancer.

BACKGROUND OF THE INVENTION

Cancer of the prostate is the most prevalent malignancy in adult males, excluding skin cancer, and is an increasingly prevalent health problem in the United States. In 1996, it was estimated that 41,400 deaths would result from this disease in the United States alone, indicating that prostate cancer is second only to lung cancer as the most common cause of death in the same population. If diagnosed and treated early, when the cancer is still confined to the prostate, the chances of cure is significantly higher.

Treatment decisions for an individual are linked to the stage of prostate cancer present in that individual. A common classification of the spread of prostate cancer was developed by the American Urological Association (AUA). The AUA system divides prostate tumors into four stages, A to D. Stage A, microscopic cancer within prostate, is further subdivided into stages A1 and A2. Sub-stage A1 is a well-differentiated cancer confined to one site within the prostate. Treatment is generally observation, radical prostatectomy, or radiation. Sub-stage A2 is a moderately to poorly differentiated cancer at multiple sites within the prostate. Treatment is radical prostatectomy or radiation. Stage B, palpable lump within the prostate, is also further subdivided into sub-stages B1 and B2. In sub-stage B1, the cancer forms a small nodule in one lobe of the prostate. In sub-stage B2, the cancer forms large or multiple nodules, or occurs in both lobes of the prostate. Treatment for sub-stages B1 and B2 is either radical prostatectomy or radiation. Stage C is a large cancer mass involving most or all of the prostate and is also further subdivided into two sub-stages. In sub-stage C1, the cancer forms a continuous mass that may have extended beyond the prostate. In sub-stage C2, the cancer forms a continuous mass that invades the surrounding tissue. Treatment for both these sub-stages is radiation with or without drugs to address the cancer. The fourth stage, Stage D is metastatic cancer and is also subdivided into two sub-stages. In sub-stage D1, the cancer appears in the lymph nodes of the pelvis. In sub-stage D2, the cancer involves tissues beyond lymph nodes. Treatment for both of these sub-stages is systemic drugs to address the cancer as well as pain.

However, current prostate cancer staging methods are limited. As many as 50% of prostate cancers initially staged as A2, B, or C are actually stage D, metastatic. Discovery of metastasis is significant because patients with metastatic cancers have a poorer prognosis and require significantly different therapy than those with localized cancers. The five year survival rates for patients with localized and metastatic prostate cancers are 93% and 29%, respectively.

Accordingly, there is a great need for more sensitive and accurate methods for the staging of a cancer in a human to determine whether or not such cancer has metastasized and for monitoring the progress of a cancer in a human which has not metastasized for the onset of metastasis.

It has now been found that a number of proteins in the public domain are useful as diagnostic markers for prostate cancer. These diagnostic markers are referred to herein as cancer specific genes or CSGs and include, but are not limited to: Pro109 which is a human zinc-α 2-glycoprotein (Freje et al. Genomics 1993 18(3):575–587); Pro112 which is a human cysteine-rich protein with a zinc-finger motif (Liebhaber et al. Nucleic Acid Research 1990 18(13):3871–3879; WO9514772 and WO9845436); Pro111 which is a prostate-specific transglutaminase (Dubbink et al. Genomics 1998 51(3):434–444); Pro115 which is a novel serine protease with transmembrane, LDLR, and SRCR domains and maps to 21q22.3 (Paoloni-Giacobino et al. Genomics 1997 44(3):309–320; WO9837418 and WO987093); Pro110 which is a human breast carcinoma fatty acid synthase (U.S. Pat. No. 5,665,874 and WO9403599); Pro113 which is a homeobox gene, HOXB13 (Steinicki et al. J. Invest. Dermatol. 1998 111:57–63); Pro114 which is a human tetraspan NET-1 (WO9839446); and Pro118 which is a human JM27 protein (WO9845435). ESTs for these CSGs are set forth in SEQ ID NO: 1, 3, 5, 7, 9, 11, 13 and 15 while the full length contigs for these CSGs are set forth in SEQ ID NO:2, 4, 6, 8, 10, 12, 14 and 16, respectively. Additional CSGs for use in the present invention are depicted herein in SEQ ID NO: 17, 18, 19 and 20.

In the present invention, methods are provided for detecting, diagnosing, monitoring, staging, prognosticating, imaging and treating prostate cancer via the cancer specific genes referred to herein as CSGs. For purposes of the present invention, CSG refers, among other things, to native protein expressed by the gene comprising a polynucleotide sequence of SEQ ID NO:1, 2, 3, 4, 5, 6, 7, 8, 9, 10, 11, 12, 13, 14, 15, 16, 17, 18, 19 or 20. By "CSG" it is also meant herein polynucleotides which, due to degeneracy in genetic coding, comprise variations in nucleotide sequence as compared to SEQ ID NO: 1–20, but which still encode the same protein. In the alternative, what is meant by CSG as used herein, means the native mRNA,encoded by the gene comprising the polynucleotide sequence of SEQ ID NO:1, 2, 3, 4, 5, 6, 7, 8, 9, 10, 11, 12, 13, 14, 15, 16, 17, 18, 19 or 20, levels of the gene comprising the polynucleotide sequence of SEQ ID NO:1, 2, 3, 4, 5, 6, 7, 8, 9, 10, 11, 12, 13, 14, 15, 16, 17, 18, 19 or 20, or levels of a polynucleotide which is capable of hybridizing under stringent conditions to the antisense sequence of SEQ ID NO:1, 2, 3, 4, 5, 6, 7, 8, 9, 40, 11, 12, 13, 14, 15, 16, 17, 18, 19 or 20.

Other objects, features, advantages and aspects of the present invention will become apparent to those of skill in the art from the following description. It should be understood, however, that the following description and the specific examples, while indicating preferred embodiments of the invention are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide a method for diagnosing the presence of prostate cancer by analyzing for changes in levels of CSG in cells, tissues or bodily fluids compared with levels of CSG in preferably the same cells, tissues, or bodily fluid type of a normal human control, wherein a change in levels of CSG in the patient versus the normal human control is associated with prostate cancer.

Further provided is a method of diagnosing metastatic prostate cancer in a patient having prostate cancer which is not known to have metastasized by identifying a human patient suspected of having prostate cancer that has metastasized; analyzing a sample of cells, tissues, or bodily fluid from such patient for CSG; comparing the CSG levels in such cells, tissues, or bodily fluid with levels of CSG in preferably the same cells, tissues, or bodily fluid type of a normal human control, wherein an increase in CSG levels in the patient versus the normal human control is associated with prostate cancer which has metastasized.

Also provided by the invention is a method of staging prostate cancer in a human which has such cancer by identifying a human patient having such cancer; analyzing a sample of cells, tissues, or bodily fluid from such patient for CSG; comparing CSG levels in such cells, tissues, or bodily fluid with levels of CSG in preferably the same cells, tissues, or bodily fluid type of a normal human control sample, wherein an increase in CSG levels in the patient versus the normal human control is associated with a cancer which is progressing and a decrease in the levels of CSG is associated with a cancer which is regressing or in remission.

Further provided is a method of monitoring prostate cancer in a human having such cancer for the onset of metastasis. The method comprises identifying a human patient having such cancer that is not known to have metastasized; periodically analyzing a sample of cells, tissues, or bodily fluid from such patient for CSG; comparing the CSG levels in such cells, tissue, or bodily fluid with levels of CSG in preferably the same cells, tissues, or bodily fluid type of a normal human control sample, wherein an increase in CSG levels in the patient versus the normal human control is associated with a cancer which has metastasized.

Further provided is a method of monitoring the change in stage of prostate cancer in a human having such cancer by looking at levels of CSG in a human having such cancer. The method comprises identifying a human patient having such cancer; periodically analyzing a sample of cells, tissues, or bodily fluid from such patient for CSG; comparing the CSG levels in such cells, tissue, or bodily fluid with levels of CSG in preferably the same cells, tissues, or bodily fluid type of a normal human control sample, wherein an increase in CSG levels in the patient versus the normal human control is associated with a cancer which is progressing and a decrease in the levels of CSG is associated with a cancer which is regressing or in remission.

Further provided are methods of designing new therapeutic agents targeted to a CSG for use in imaging and treating prostate cancer. For example, in one embodiment, therapeutic agents such as antibodies targeted against CSG or fragments of such antibodies can be used to detect or image localization of CSG in a patient for the purpose of detecting or diagnosing a disease or condition. Such antibodies can be polyclonal, monoclonal, or omniclonal or prepared by molecular biology techniques. The term "antibody", as used herein and throughout the instant specification is also meant to include aptamers and single-stranded oligonucleotides such as those derived from an in vitro evolution protocol referred to as SELEX and well known to those skilled in the art. Antibodies can be labeled with a variety of detectable labels including, but not limited to, radioisotopes and paramagnetic metals. Therapeutics agents such as antibodies or fragments thereof can also be used in the treatment of diseases characterized by expression of CSG. In these applications, the antibody can be used without or with derivatization to a cytotoxic agent such as a radioisotope, enzyme, toxin, drug or a prodrug.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DETAILED DESCRIPTION OF THE INVENTION

The present invention relates to diagnostic assays and methods, both quantitative and qualitative for detecting, diagnosing, monitoring, staging and prognosticating cancers by comparing levels of CSG in a human patient with those of CSG in a normal human control. For purposes of the present invention, what is meant be CSG levels is, among other things, native protein expressed by the gene comprising a polynucleotide sequence of SEQ ID NO:1, 2, 3, 4, 5, 6, 7, 8, 9, 10, 11, 12, 13, 14, 15, 16, 17, 18, 19 or 20. By "CSG" it is also meant herein polynucleotides which, due to degeneracy in genetic coding, comprise variations in nucleotide sequence as compared to SEQ ID NO: 1–20, but which still encode the same protein. The native protein being detected, may be whole, a, breakdown product, a complex of molecules or chemically modified. In the alternative, what is meant by CSG as used herein, means the native mRNA encoded by the gene comprising the polynucleotide sequence of SEQ ID NO:1, 2, 3, 4, 5, 6, 7, 8, 9, 10, 11, 12, 13, 14, 15, 16, 17, 18, 19 or 20, levels of the gene comprising the polynucleotide sequence of SEQ ID NO:1, 2, 3, 4, 5, 6, 7, 8, 9, .10, 11, 12, 13, 14, 15, 16, 17, 18, 19 or 20, or levels of a polynucleotide which is capable of hybridizing under stringent conditions to the antisense sequence of SEQ ID NO:1, 2, 3, 4, 5, 6, 7, 8, 9, 10, 11, 12, 13, 14, 15, 16, 17, 18, 19 or 20. Such levels are preferably determined in at least one of, cells, tissues and/or bodily fluids, including determination of normal and abnormal levels. Thus, for instance, a diagnostic assay in accordance with the invention for diagnosing overexpression of CSG protein compared to normal control bodily fluids, cells, or tissue samples may be used to diagnose the presence of prostate cancer.

All the methods of the present invention may optionally include determining the levels of other cancer markers as well as CSG. Other cancer markers, in addition to CSG, useful in the present invention will depend on the cancer being tested and are known to those of skill in the art.

Diagnostic Assays

The present invention provides methods for diagnosing the presence of prostate cancer by analyzing for changes in levels of CSG in cells, tissues or bodily fluids compared with levels of CSG in cells, tissues or bodily fluids of preferably the same type from a normal human control, wherein an increase in levels of CSG in the patient versus the normal human control is associated with the presence of prostate cancer.

Without limiting the instant invention, typically, for a quantitative diagnostic assay a positive result indicating the patient being tested has cancer is one in which cells, tissues or bodily fluid levels of the cancer marker, such as CSG, are at least two times higher, and most preferably are at least five times higher, than in preferably the same cells, tissues or bodily fluid of a normal human control.

The present invention also provides a method of diagnosing metastatic prostate cancer in a patient having prostate cancer which has not yet metastasized for the onset of metastasis. In the method of the present invention, a human cancer patient suspected of having prostate cancer which may have metastasized (but which was not previously known to have metastasized) is identified. This is accomplished by a variety of means known to those of skill in the art.

In the present invention, determining the presence of CSG levels in cells, tissues or bodily fluid, is particularly useful for discriminating between prostate cancer which has not metastasized and prostate cancer which has metastasized. Existing techniques have difficulty discriminating between prostate cancer which has metastasized and prostate cancer which has not metastasized and proper treatment selection is often dependent upon such knowledge.

In the present invention, the cancer marker levels measured in such cells, tissues or bodily fluid is CSG, and are compared with levels of CSG in preferably the same cells, tissue or bodily fluid type of a normal human control. That is, if the cancer marker being observed is just CSG in serum, this level is preferably compared with the level of CSG in serum of a normal human control. An increase in the CSG in the patient versus the normal human control is associated with prostate cancer which has metastasized.

Without limiting the instant invention, typically, for a quantitative diagnostic assay a positive result indicating the cancer in the patient being tested or monitored has metastasized is one in which cells, tissues or bodily fluid levels of the cancer marker, such as CSG, are at least two times higher, and most preferably are at least five times higher, than in preferably the same cells, tissues or bodily fluid of a normal patient.

Normal human control as used herein includes a human patient without cancer and/or non cancerous samples from the patient; in the methods for diagnosing or monitoring for metastasis, normal human control may preferably also include samples from a human patient that is determined by reliable methods to have prostate cancer which has not metastasized.

Staging

The invention also provides a method of staging prostate cancer in a human patient. The method comprises identifying a human patient having such cancer and analyzing cells, tissues or bodily fluid from such human patient for CSG. The CSG levels determined in the patient are then compared with levels of CSG in preferably the same cells, tissues or bodily fluid type of a normal human control, wherein an increase in CSG levels in the human patient versus the normal human control is associated with a cancer which is progressing and a decrease in the levels of CSG (but still increased over true normal levels) is associated with a cancer which is regressing or in remission.

Monitoring

Further provided is a method of monitoring prostate cancer in a human patient having such cancer for the onset of metastasis. The method comprises identifying a human patient having such cancer that is not known to have metastasized; periodically analyzing cells, tissues or bodily fluid from such human patient for CSG; and comparing the CSG levels determined in the human patient with levels of CSG in preferably the same cells, tissues or bodily fluid type of a normal human control, wherein an increase in CSG levels in the human patient versus the normal human control is associated with a cancer which has metastasized. In this method, normal human control samples may also include prior patient samples.

Further provided by this invention is a method of monitoring the change in stage of prostate cancer in a human patient having such cancer. The method comprises identifying a human patient having such cancer; periodically analyzing cells, tissues or bodily fluid from such human patient for CSG; and comparing the CSG levels determined in the human patient with levels of CSG in preferably the same cells, tissues or bodily fluid type of a normal human control, wherein an increase in CSG levels in the human patient versus the normal human control is associated with a cancer which is progressing in stage and a decrease in the levels of CSG is associated with a cancer which is regressing in stage or in remission. In this method, normal human control samples may also include prior patient samples.

Monitoring a patient for onset of metastasis is periodic and preferably done on a quarterly basis. However, this may be more or less frequent depending on the cancer, the particular patient, and the stage of the cancer.

Assay Techniques

Assay techniques that can be used to determine levels of gene expression (including protein levels), such as CSG of the present invention, in a sample derived from a patient are well known to those of skill in the art. Such assay methods include, without limitation, radioimmunoassays, reverse transcriptase PCR (RT-PCR) assays, immunohistochemistry assays, in situ hybridization assays, competitive-binding assays, Western Blot analyses, ELISA assays and proteomic approaches: two-dimensional gel electrophoresis (2D electrophoresis) and non-gel based approaches such as mass spectrometry or protein interaction profiling. Among these, ELISAs are frequently preferred to diagnose a gene's expressed protein in biological fluids.

An ELISA assay initially comprises preparing an antibody, if not readily available from a commercial source, specific to CSG, preferably a monoclonal antibody. In addition a reporter antibody generally is prepared which binds specifically to CSG. The reporter antibody is attached to a detectable reagent such as radioactive, fluorescent or enzymatic reagent, for example horseradish peroxidase enzyme or alkaline phosphatase.

To carry out the ELISA, antibody specific to CSG is incubated on a solid support, e.g. a polystyrene dish, that binds the antibody. Any free protein binding sites on the dish are then covered by incubating with a non-specific protein such as bovine serum albumin. Next, the sample to be analyzed is incubated in the dish, during which time CSG binds to the specific antibody attached to the polystyrene dish. Unbound sample is washed out with buffer. A reporter antibody specifically directed to CSG and linked to a detectable reagent such as horseradish peroxidase is placed in the dish resulting in binding of the reporter antibody to any monoclonal antibody bound to CSG. Unattached reporter antibody is then washed out. Reagents for peroxidase activity, including a calorimetric substrate are then added to the dish. Immobilized peroxidase, linked to CSG antibodies, produces a colored reaction product. The amount of color developed in a given time period is proportional to the amount of CSG protein present in the sample. Quantitative results typically are obtained by reference to a standard curve.

A competition assay can also be employed wherein antibodies specific to CSG are attached to a solid support and labeled CSG and a sample derived from the host are passed over the solid support. The amount of label detected which is attached to the solid support can be correlated to a quantity of CSG in the sample.

Nucleic acid methods can also be used to detect CSG mRNA as a marker for prostate cancer. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e. gridding) can be used to both detect the expression of and quantitate the level of expression of that gene. In this approach, a cDNA encoding the CSG gene is fixed to a substrate. The substrate may be of any suitable type including but not limited to glass, nitrocellulose, nylon or plastic. At least a portion of the DNA encoding the CSG gene is attached to the substrate and then incubated with the analyte, which may be RNA or a complementary DNA (cDNA) copy of the RNA, isolated from the tissue of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

Of the proteomic approaches, 2D electrophoresis is a technique well known to those in the art. Isolation of individual proteins from a sample such as serum is accomplished using sequential separation of proteins by different characteristics usually on polyacrylamide gels. First, proteins are separated by size using an electric current. The current acts uniformly on all proteins, so smaller proteins move farther on the gel than larger proteins. The second dimension applies a current perpendicular to the first and separates proteins not on the basis of size but on the specific electric charge carried by each protein. Since no two proteins with different sequences are identical on the basis of both size and charge, the result of a 2D separation is a square gel in which each protein occupies a unique spot. Analysis of the spots with chemical or antibody probes, or subsequent protein microsequencing can reveal the relative abundance of a given protein and the identity of the proteins in the sample.

The above tests can be carried out on samples derived from a variety of cells, bodily fluids and/or tissue extracts such as homogenates or solubilized tissue obtained from a patient. Tissue extracts are obtained routinely from tissue biopsy and autopsy material. Bodily fluids useful in the present invention include blood, urine, saliva or any other bodily secretion or derivative thereof. By blood it is meant to include whole blood, plasma, serum or any derivative of blood.

In Vivo Targeting of CSGs

Identification of these CSGs is also useful in the rational design of new therapeutics for imaging and treating cancers, and in particular prostate cancer. For example, in one embodiment, antibodies which specifically bind to CSG can be raised and used in vivo in patients suspected of suffering from prostate cancer. Antibodies which specifically bind a CSG can be injected into a patient suspected of having prostate cancer for diagnostic and/or therapeutic purposes. The preparation and use of antibodies for in vivo diagnosis is well known in the art. For example, antibody-chelators labeled with Indium-111 have been described for use in the radioimmunoscintographic imaging of carcinoembryonic antigen expressing tumors (Sumerdon et al. Nucl. Med. Biol. 1990 17:247–254). In particular, these antibody-chelators have been used in detecting tumors in patients suspected of having recurrent colorectal cancer (Griffin et al. J. Clin. Onc. 1991 9:631–640). Antibodies with paramagnetic ions as labels for use in magnetic resonance imaging have also been described (Lauffer, R. B. Magnetic Resonance in Medicine 1991 22:339–342). Antibodies directed against CSG can be used in a similar manner. Labeled antibodies which specifically bind CSG can be injected into patients suspected of having prostate cancer for the purpose of diagnosing or staging of the disease status of the patient. The label used will be selected in accordance with the imaging modality to be used. For example, radioactive labels such as Indium-111, Technetium-99m or Iodine-131 can be used for planar scans or single photon emission computed tomography (SPECT). Positron emitting labels such as Fluorine-19 can be used in positron emission tomography. Paramagnetic ions such as Gadlinium (III) or Manganese (II) can be used in magnetic resonance imaging (MRI). Localization of the label permits determination of the spread of the cancer. The amount of label within an organ or tissue also allows determination of the presence or absence of cancer in that organ or tissue.

For patients diagnosed with prostate cancer, injection of an antibody which specifically binds CSG can also have a therapeutic benefit. The antibody may exert its therapeutic effect alone. Alternatively, the antibody can be conjugated to a cytotoxic agent such as a drug, toxin or radionuclide to enhance its therapeutic effect. Drug monoclonal antibodies have been described in the art for example by Garnett and Baldwin, Cancer Research 1986 46:2407–2412. The use of toxins conjugated to monoclonal antibodies for the therapy of various cancers has also been described by Pastan et al. Cell 1986 47:641–648. Yttrium-90 labeled monoclonal antibodies have been described for maximization of dose delivered to the tumor while limiting toxicity to normal tissues (Goodwin and Meares Cancer Supplement 1997 80:2675–2680). Other cytotoxic radionuclides including, but not limited to Copper-67, Iodine-131 and Rhenium-186 can also be used for labeling of antibodies against CSG.

Antibodies which can be used in these in vivo methods include polyclonal, monoclonal and omniclonal antibodies and antibodies prepared via molecular biology techniques. Antibody fragments and aptamers and single-stranded oligonucleotides such as those derived from an in vitro evolution protocol referred to as SELEX and well known to those skilled in the art can also be used.

Small molecules predicted via computer imaging to specifically bind to regions of CSGs can also be designed and synthesized and tested for use in the imaging and treatment of prostate cancer. Further, libraries of molecules can be screened for potential anticancer agents by assessing the ability of the molecule to bind to CSGs identified herein. Molecules identified in the library as being capable of binding to CSG are key candidates for further evaluation for use in the-treatment of prostate cancer.

EXAMPLES

The present invention is further described by the following examples. These examples are provided solely to illustrate the invention by reference to specific embodiments. These exemplifications, while illustrating certain aspects of the invention, do not portray the limitations or circumscribe the scope of the disclosed invention.

All examples outlined here were carried out using standard techniques, which are well known and routine to those of skill in the art, except where otherwise described in detail. Routine molecular biology techniques of the following example can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Example 1

Identification of CSGs

Identification of CSGs were carried out by a systematic analysis of data in the LIFESEQ database available from Incyte Pharmaceuticals, Palo Alto, Calif., using the data mining Cancer Leads Automatic Search Package (CLASP) developed by diaDexus LLC, Santa Clara, Calif.

The CLASP performs the following steps: selection of highly expressed organ specific genes based on the abundance level of the corresponding EST in the targeted organ versus all the other organs; analysis of the expression level of each highly expressed organ specific genes in normal, tumor tissue, disease tissue and tissue libraries associated with tumor or disease; selection of the candidates demonstrating component ESTs were exclusively or more frequently found in tumor libraries. The CLASP allows the identification of highly expressed organ and cancer specific genes. A final manual in depth evaluation is then performed to finalize the CSGs selection.

Clones depicted in the following Table 1 are CSGs useful in diagnosing, monitoring, staging, imaging and treating prostate cancer.

TABLE 1

| CSGs | | |
|---|---|---|
| Clone ID | Pro # | SEQ ID NO: |
| 3424528H1 | Pro109 | 1,2 |
| 578349H1 | Pro112 | 3,4 |
| 1794013H1 | Pro111 | 5,6 |
| 2189835H1 | Pro115 | 7,8 |
| 3277219H1 | Pro110 | 9,10 |
| 1857415 | Pro113 | 11,12 |
| 1810463H1 | Pro114 | 13,14 |
| zr65G11 | Pro118 | 15,16 |
| 2626135H1 | | 17 |
| zd46d08 | | 18 |
| 1712252H1 | | 19 |
| 784583H1 | | 20 |

Example 2

Relative Quantitation of Gene Expression

Real-Time quantitative PCR with fluorescent Taqman probes is a quantitation detection system utilizing the 5'–3' nuclease activity of Taq DNA polymerase. The method uses an internal fluorescent oligonucleotide probe (Taqman) labeled with a 5' reporter dye and a downstream, 3' quencher dye. During PCR, the 5'–3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH), ATPase, or 18S ribosomal RNA (rRNA) is used as this endogenous control. To calculate relative quantitation between all the samples studied, the target RNA levels for one sample were used as the basis for comparative results (calibrator). Quantitation relative to the "calibrator" can be obtained using the standard curve method or the comparative method (User Bulletin #2: ABI PRISM 7700 Sequence Detection System)

The tissue distribution and the level of the target gene were evaluated for every sample in normal and cancer tissues. Total RNA was extracted from normal tissues, cancer tissues, and from cancers and the corresponding matched adjacent tissues. Subsequently, first strand cDNA was prepared with reverse transcriptase and the polymerase chain reaction was done using primers and Taqman probes specific to each target gene. The results were analyzed using the ABI PRISM 7700 Sequence Detector. The absolute numbers are relative levels of expression of the target gene in a particular tissue compared to the calibrator tissue.

Expression of Clone ID 3424528H1 (Pro109)

For the CSG Pro109, real-time quantitative PCR was performed using the following primers:

Forward Primer:

5'-ATCAGAACAAAGAGGCTGTGTC-3'  (SEQ ID NO:21)

Reverse Primer:

5'-ATCTCTAAAGCCCCAACCTTC-3'  (SEQ ID NO:22)

The absolute numbers depicted in Table 2 are relative levels of expression of the CSG referred to as Pro109 in 12 normal different tissues. All the values are compared to normal stomach (calibrator). These RNA samples are commercially available pools, originated by pooling samples of a particular tissue from different individuals.

TABLE 2

| Relative Levels of CSG Pro109 Expression in Pooled Samples | |
|---|---|
| Tissue | NORMAL |
| Colon | 0.02 |
| Endometrium | 0.01 |
| Kidney | 0.48 |
| Liver | 14.83 |
| Ovary | 0.08 |
| Pancreas | 4.38 |
| Prostate | 11.24 |
| Small Intestine | 0.42 |
| Spleen | 0 |
| Stomach | 1 |
| Testis | 0.62 |
| Uterus | 0.02 |

The relative levels of expression in Table 2 show that with the exception of liver (14.83), Pro109 mRNA expression is higher (11.24) in prostate compared with all other normal tissues analyzed. Pancreas, with a relative expression level of 4.38, is the only other tissue expressing considerable mRNA for Pro109.

The absolute numbers in Table 2 were obtained analyzing pools of samples of a particular tissue from different individuals. They cannot be compared to the absolute numbers originated from RNA obtained from tissue samples of a single individual in Table 3.

The absolute numbers depicted in Table 3 are relative levels of expression of Pro109 in 28 pairs of matching samples and 4 unmatched samples. All the values are compared to normal stomach (calibrator). A matching pair is formed by mRNA from the cancer sample for a particular tissue and mRNA from the normal adjacent sample for that same tissue from the same individual.

TABLE 3

Relative Levels of CSG Pro109 Expression in Individual Samples

| Sample ID | Tissue | Cancer | Matching Normal Adjacent |
|---|---|---|---|
| Pro34B | Prostate 1 | 5.98 | 6.06 |
| Pro65XB | Prostate 2 | 16.68 | 3.85 |
| Pro69XB | Prostate 3 | 20.46 | 6.82 |
| Pro78XB | Prostate 4 | 1.39 | 1.4 |
| Pro101XB | Prostate 5 | 24.8 | 9.8 |
| Pro12B | Prostate 6 | 9.1 | 0.2 |
| Pro13XB | Prostate 7 | 0.5 | 9.7 |
| Pro20XB | Prostate 8 | 13 | 12.5 |
| Pro23B | Prostate 9 | 16.8 | 3 |
| Ovr10005O | Ovary 1 | 0.4 | |
| Ovr1028 | Ovary 2 | 1.9 | |
| Ovr18GA | Ovary 3 | | 0.1 |
| Ovr206I | Ovary 4 | | 0.1 |
| Mam12X | Mammary Gland 1 | 13.5 | 1.4 |
| Mam47XP | Mammary Gland 2 | 0.7 | 0.2 |
| Lng47XQ | Lung 1 | 2.36 | 0.03 |
| Lng60XL | Lung 2 | 7.39 | 0.2 |
| Lng75XC | Lung 3 | 0.77 | 0.27 |
| StoAC44 | Stomach 1 | 0.05 | 1.19 |
| StoAC93 | Stomach 2 | 0.55 | 0.8 |
| StoAC99 | Stomach 3 | 0.12 | 3.04 |
| ColAS43 | Colon 1 | 16.11 | 0.07 |
| ColAS45 | Colon 2 | 0.11 | 0.08 |
| ColAS46 | Colon 3 | 4.99 | 0.4 |
| Liv15XA | Liver 1 | 8.43 | 10.97 |
| Liv42X | Liver 2 | 1.57 | 20.82 |
| Liv94XA | Liver 3 | 2.98 | 9.19 |
| Pan77X | Pancreas 1 | 36 | 32 |
| Pan82XP | Pancreas 2 | 0.09 | 7.09 |
| Pan92X | Pancreas 3 | 0.7 | 0 |
| Pan71XL | Pancreas 4 | 2.48 | 0.73 |
| Pan10343 | Pancreas 5 | 46 | 5.5 |

0 = Negative

In the analysis of matching samples, the higher levels of expression were in prostate, showing a high degree of tissue specificity for prostate tissue. Of all the samples different than prostate analyzed, only 4 cancer samples (the cancer sample mammary 1 with 13.5, colon 1 with 16.11, liver 1 with 8.43, and lung 2 with 7.39) showed an expression comparable to the mRNA expression in prostate. These results confirmed some degree of tissue specificity as obtained with the panel of normal pooled samples (Table 2).

Furthermore, the level of MRNA expression was compared in cancer samples and the isogenic normal adjacent tissue from the same individual. This comparison provides an indication of specificity for the cancer (e.g. higher levels of mRNA expression in the cancer sample compared to the normal adjacent). Table 3 shows overexpression of Pro109 in 6 out of 9 primary prostate cancer tissues compared with their respective normal adjacents. Thus, overepression in the cancer tissue was observed in 66.66% of the prostate matching samples tested (total of 9 prostate matching samples).

Altogether, the degree of tissue specificity, plus the mRNA overexpression in 66.66% of the primary prostate matching samples tested is indicative of Pro109 being a diagnostic marker for prostate cancer.

Expression of Clone ID 578349H1 (Pro112)

For the CSG Pro112, real-time quantitative PCR was performed using the following primers:

Forward Primer

5'-TGCCGAAGAGGTTCAGTGC-3'  (SEQ ID NO:23)

Reverse Primer

5'-GCCACAGTGGTACTGTCCAGAT-3'  (SEQ ID NO:24)

The absolute numbers depicted in Table 4 are relative levels of expression of the CSG Pro112 in 12 normal different tissues. All the values are compared to normal thymus (calibrator). These RNA samples are commercially available pools, originated by pooling samples of a particular tissue from different individuals.

TABLE 4

Relative Levels of CSG Pro112 Expression in Pooled Samples

| Tissue | NORMAL |
|---|---|
| Brain | 2.9 |
| Heart | 0.1 |
| Kidney | 0.2 |
| Liver | 0.2 |
| Lung | 7.7 |
| Mammary | 4.2 |
| Muscle | 0.1 |
| Prostate | 5.5 |
| Small Intestine | 1.8 |
| Testis | 1 |
| Thymus | 1 |
| Uterus | 21 |

The relative levels of expression in Table 4 show that Pro112 mRNA expression is the $3^{rd}$ most highly expressed gene (after uterus and mammary) in the pool of normal prostate tissue compared to a total of 12 tissues analyzed. The absolute numbers in Table 4 were obtained analyzing pools of samples of a particular tissue from different individuals. These results demonstrate that Pro112 mRNA expression is specific for prostate thus indicating Pro112 to be a diagnostic marker for prostate disease especially cancer.

Expression of Clone ID 1794013H1 (Pro111)

For the CSG Pro111, real-time quantitative PCR was performed using the following primers:

Forward Primer

5'-GCTGCAAGTTCTCCACATTGA-3'  (SEQ ID NO:25)

Reverse Primer

5'-CAGCCGCAGGTGAAACAC-3'  (SEQ ID NO:26)

The absolute numbers depicted in Table 5 are relative levels of expression of the CSG Pro111 in 12 normal different tissues. All the values are compared to normal testis (calibrator). These RNA samples are commercially available pools, originated by pooling samples of a particular tissue from different individuals.

TABLE 5

Relative Levels of CSG Pro111 Expression in Pooled Samples

| Tissue | NORMAL |
|---|---|
| Brain | 0.04 |
| Heart | 0 |
| Kidney | 0 |
| Liver | 0 |

TABLE 5-continued

Relative Levels of CSG Pro111 Expression in Pooled Samples

| Tissue | NORMAL |
|---|---|
| Lung | 0.05 |
| Mammary | 0.14 |
| Muscle | 5166.6 |
| Prostate | 1483.72 |
| Small Intestine | 0.33 |
| Testis | 1 |
| Thymus | 0.49 |
| Uterus | 0.07 |

The relative levels of expression in Table 5 show that Pro111 mRNA expression is extraordinarily high in the pool of normal prostate (1483.72) compared to all the other tissues analyzed with the exception of muscle (5166.6). These results demonstrate that Pro111 mRNA expression shows specificity for prostate and muscle.

The absolute numbers in Table 5 were obtained analyzing pools of samples of a particular tissue from different individuals. They cannot be compared to the absolute numbers originated from RNA obtained from tissue samples of a single individual in Table 6.

The absolute numbers depicted in Table 6 are relative levels of expression of Pro111 in 48 pairs of matching and 18 unmatched samples. All the values are compared to normal testis (calibrator). A matching pair is formed by mRNA from the cancer sample for a particular tissue and mRNA from the normal adjacent sample for that same tissue from the same individual.

TABLE 6

Relative Levels of CSG Pro111 Expression in Individual Samples

| Sample ID | Tissue | Cancer | Matching Normal Adjacent |
|---|---|---|---|
| Pro101XB | Prostate 1 | 8.3 | 21.8 |
| Pro12B | Prostate 2 | 2336 | 133 |
| Pro13XB | Prostate 3 | 3.4 | 23 |
| Pro20XB | Prostate 4 | 21.6 | 121.5 |
| Pro23B | Prostate 5 | 19.4 | 3.7 |
| Pro34B | Prostate 6 | 15 | 39 |
| Pro65XB | Prostate 7 | 8 | 867 |
| Pro69XB | Prostate 8 | 56 | 94 |
| Pro78XB | Prostate 9 | 24 | 1515 |
| Pro84XB | Prostate 10 | 119 | 15.35 |
| Pro90XB | Prostate 11 | 8.08 | 112.2 |
| Pro91XB | Prostate 12 | 0.88 | 51.8 |
| ProC215 | Prostate 13 | 0.3 | |
| ProC234 | Prostate 14 | 0.35 | |
| ProC280 | Prostate 15 | 436.5 | |
| Pro109XB | Prostate 16 | 3.43 | 265 |
| Pro110 | Prostate 17 | 18.2 | 8.73 |
| Pro125XB | Prostate 18 | 0.34 | 186 |
| Pro326 | Prostate 19 | 1392 | 110 |
| Pro10R | Prostate 20 (prostatitis) | 0.5 | |
| Pro20R | Prostate 21 (prostatitis) | 24.1 | |
| Pro258 | Prostate 22 (BPH) | 4610 | |
| Pro263C | Prostate 23 (BPH) | 0 | |
| Pro267A | Prostate 24 (BPH) | 1.46 | |
| Pro271A | Prostate 25 (BPH) | 0 | |
| Pro460Z | Prostate 26 (BPH) | 1.47 | |
| ProC032 | Prostate 27 (BPH) | 14.4 | |
| Tst39X | Testis 1 | 0 | 0 |
| Bld32XK | Bladder 1 | 0.44 | 0.41 |
| Bld46XK | Bladder 2 | 0 | 0 |
| Bld66X | Bladder 3 | 0 | 0 |
| BldTR14 | Bladder 4 | 0 | 0 |
| Kid106XD | Kidney 1 | 0 | 0 |
| Kid107XD | Kidney 2 | 0 | 0 |
| Kid109XD | Kidney 3 | 0 | 0 |
| Pan10343 | Pancreas 1 | 0 | 0 |
| Pan71XL | Pancreas 2 | 0 | 0 |
| Pan77X | Pancreas 3 | 0 | 0 |
| Liv15XA | Liver 1 | 0 | 0 |
| Liv42X | Liver 2 | 0 | 0 |
| ClnAS43 | Colon 1 | 0 | 0 |
| ClnAS45 | Colon 2 | 0 | 0 |
| ClnAS46 | Colon 3 | 0 | 0 |
| ClnAS67 | Colon 4 | 0 | 0 |
| ClnAC19 | Colon 5 | 0 | 0 |
| ClnAS12 | Colon 6 | 0 | 0 |
| SmI21XA | Small Intestine 1 | 0 | 0 |
| SmIH89 | Small Intestine 2 | 0 | 0 |
| Lng47XQ | Lung 1 | 0.7 | 0 |
| Lng60XL | Lung 2 | 0 | 0 |
| Lng75XC | Lung 3 | 0 | 0 |
| Lng90X | Lung 4 | 0 | 0 |
| Mam12X | Mammary Gland 1 | 0 | 1.4 |
| Mam59X | Mammary Gland 2 | 0.2 | 0 |
| MamA06X | Mammary Gland 3 | 0 | 0 |
| MamS127 | Mammary Gland 4 | 0 | 0 |
| Mam162X | Mammary Gland 5 | 0 | 0 |
| Mam42DN | Mammary Gland 6 | 0 | 0 |
| Ovr103X | Ovary 1 | 0.14 | 0 |
| Ovr1005O | Ovary 2 | 0.2 | |
| Ovr1028 | Ovary 3 | 0 | |
| Ovr104OO | Ovary 4 | 0.2 | |
| Ovr18GA | Ovary 5 | | 0 |
| Ovr206I | Ovary 6 | | 0 |
| Ovr20GA | Ovary 7 | | 0.2 |
| Ovr25GA | Ovary 8 | | 0 |

0 = Negative

In the analysis of matching samples, the higher levels of expression were in prostate showing a high degree of tissue specificity for prostate. These results confirm the tissue specificity results obtained with normal pooled samples (Table 5).

Furthermore, the level of mRNA expression in cancer samples and the isogenic normal adjacent tissue from the same individual were compared. This comparison provides an indication of specificity for cancer (e.g. higher levels of mRNA expression in the cancer sample compared to the normal adjacent). Table 6 shows overexpression of Pro111 in 5 out of 16 primary prostate cancer samples compared with their respective normal adjacent (prostate samples 2, 5, 10, 17, and 19). Similar expression levels were observed in 3 unmatched prostate cancers (prostate samples 13, 14, 15), 2 prostatitis (prostate samples 20, 21), and 6 benign prostatic hyperplasia samples (prostate samples 22 through 27). Thus, there is overexpression in the cancer tissue of 31.25% of the prostate matching samples tested (total of 16 prostate matching samples).

Altogether, the high level of tissue specificity, plus the mRNA overexpression in 31.25% of the prostate matching samples tested are indicative of Pro111 being a diagnostic marker for prostate cancer.

Expression of Clone ID 2189935H1 (Pro115)

For the CSG Pro115, real-time quantitative PCR was performed using the following primers:

Forward Primer

5'-TGGCTTTGAACTCAGGGTCA-3'     (SEQ ID NO:27)

Reverse Primer

5'-CGGATGCACCTCGTAGACAG-3'     (SEQ ID NO:28)

The absolute numbers depicted in Table 7 are relative levels of expression of the CSG Pro115 in 12 normal different tissues. All the values are compared to normal thymus (calibrator). These RNA samples are commercially available pools, originated by pooling samples of a particular tissue from different individuals.

TABLE 7

Relative Levels of CSG Pro115 Expression in Pooled Samples

| Tissue | NORMAL |
|---|---|
| Brain | 0.016 |
| Heart | 0.002 |
| Kidney | 8.08 |
| Liver | 2.20 |
| Lung | 112.99 |
| Mammary | 29.45 |
| Muscle | 0.05 |
| Prostate | 337.79 |
| Small Intestine | 7.54 |
| Testis | 1.48 |
| Thymus | 1 |
| Uterus | 1.4 |

The relative levels of expression in Table 7 show that Pro115 mRNA expression is higher (337.79) in prostate compared with all the other normal tissues analyzed. Lung, with a relative expression level of 112.99, and mammary (29.446) are the other tissues expressing moderate levels of mRNA for Pro115. These results establish Pro115 mRNA expression to be highly specific for prostate.

The absolute numbers in Table 7 were obtained analyzing pools of samples of a particular tissue from different individuals. They cannot be compared to the absolute numbers originated from RNA obtained from tissue samples of a single individual in Table 8.

The absolute numbers depicted in Table 8 are relative levels of expression of Pro115 in 17 pairs of matching and 21 unmatched samples. All the values are compared to normal thymus (calibrator). A matching pair is formed by mRNA from the cancer sample for a particular tissue and mRNA from the normal adjacent sample for that same tissue from the same individual.

TABLE 6

Relative Levels of CSG Pro115 Expression in Individual Samples

| Sample ID | Tissue | Cancer | Matching Normal Adjacent |
|---|---|---|---|
| Pro12B | Prostate 1 | 1475.9 | 190.3 |
| ProC234 | Prostate 2 | 169.61 | |
| Pro109XB | Prostate 3 | | 639.53 |
| Pro101XB | Prostate 4 | 1985.2 | 2882.9 |
| Pro13XB | Prostate 5 | 34.9 | 13.9 |
| Pro215 | Prostate 6 | 525.59 | |
| Pro125XB | Prostate 7 | | 556.05 |
| Pro23B | Prostate 8 | 1891.4 | 1118.6 |
| ProC280 | Prostate 9 | 454.3 | |
| Pro20XB | Prostate 10 | 1332.6 | |
| Pro34B | Prostate 11 | | 362.91 |

TABLE 6-continued

Relative Levels of CSG Pro115 Expression in Individual Samples

| Sample ID | Tissue | Cancer | Matching Normal Adjacent |
|---|---|---|---|
| Pro65XB | Prostate 12 | | 135.06 |
| Pro69XB | Prostate 13 | | 179.67 |
| Pro10R | Prostate 14 (prostatitis) | 143.82 | |
| Pro20R | Prostate 15 (prostatitis) | 397.79 | |
| Pro25S | Prostate 16 (BPH) | 216.6 | |
| Pro263C | Prostate 17 (BPH) | 601.25 | |
| Pro267A | Prostate 18 (BPH) | 200.28 | |
| Pro271A | Prostate 19 (BPH) | 111.43 | |
| Pro460Z | Prostate 20 (BPH) | 53.84 | |
| ProC032 | Prostate 21 (BPH) | 56.94 | |
| SmI21XA | Small Intestine 1 | 28.8 | 29.9 |
| SmIH89 | Small Intestine 2 | 70.8 | 348.5 |
| ClnAC19 | Colon 1 | 22.73 | 446.47 |
| ClnAS12 | Colon 2 | 116.97 | 493.18 |
| Kid106XD | Kidney 1 | 86.13 | 41.14 |
| Kid107XD | Kidney 2 | 0.26 | 35.14 |
| Lng47XQ | Lung 1 | 5.13 | 20.98 |
| Lng60XL | Lung 2 | 13.93 | 114.78 |
| Lng75XC | Lung 3 | 16.47 | 53.79 |
| Mam12X | Mammary Gland 1 | 6.25 | 10.75 |
| Mam162X | Mammary Gland 2 | 1.84 | 2.54 |
| Mam42DN | Mammary Gland 3 | 23.08 | 35.51 |
| Ovr10050 | Ovary 1 | 0.9 | |
| Ovr1028 | Ovary 2 | 261.4 | |
| Ovr103X | Ovary 3 | 7 | 0.1 |
| Ovr20GA | Ovary 4 | | 0 |
| Ovr25GA | Ovary 5 | | 0 |

0 = Negative

Higher levels of expression were seen in prostate, showing a high degree of tissue specificity for prostate tissue. Of all the analyzed samples different from prostate, only two cancer samples (colon 2 with 116.97 and ovary 2 with 261.4), and 5 normal adjacent tissue samples (small intestine 2, colon 1, colon 2, kidney 1, and lung 2), showed an expression comparable to the mRNA expression in prostate. These results confirmed the tissue specificity results obtained with the panel of normal pooled samples (Table 7).

Furthermore, the levels of mRNA expression in cancer samples and the isogenic normal adjacent tissue from the same individual were compared. This comparison provides an indication of specificity for the cancer (e.g. higher levels of mRNA expression in the cancer sample compared to the normal adjacent). Table 8 shows higher expression of Pro115 in 3 out of 4 matched prostate cancer tissues (prostate samples 1, 5 & 8).

Altogether, the high level of tissue specificity, plus the higher expression in 75% of the prostate matching samples tested, are indicative of Pro115 being a diagnostic marker for prostate cancer.

Expression of Clone ID 3277219H1 (Pro110)

For the CSG Pro110, real-time quantitative PCR was performed using the following primers:

Forward Primer

5'-CGGCAACCTGGTAGTGAGTG-3'     (SEQ ID NO:29)

Reverse Primer

5'-CGCAGCTCCTTGTAAACTTCAG-3'     (SEQ ID NO:30)

The absolute numbers depicted in Table 9 are relative levels of expression of the CSG Pro110 in 12 normal different tissues. All the values are compared to normal small intestine (calibrator). These RNA samples are commercially available pools, originated by pooling samples of a particular tissue from different individuals.

TABLE 9

Relative Levels of CSG Pro110 Expression in Pooled Samples

| Tissue | NORMAL |
|---|---|
| Brain | 6.61 |
| Heart | 0.7 |
| Kidney | 0.74 |
| Liver | 7.94 |
| Lung | 11.88 |
| Mammary | 22.78 |
| Muscle | 6.77 |
| Prostate | 3.01 |
| Small Intestine | 1 |
| Testis | 2.58 |
| Thymus | 13.74 |
| Uterus | 2.61 |

The relative levels of expression in Table 9 show that Pro110 mRNA expression is not as high in normal prostate (3.01) compared with all the other normal tissues analyzed.

The absolute numbers in Table 9 were obtained analyzing pools of samples of a particular tissue from different individuals. They cannot be compared to the absolute numbers originated from RNA obtained from tissue samples of a single individual in Table 10.

The absolute numbers depicted in Table 10 are relative levels of expression of Pro110 in 33 pairs of matching samples. All the values are compared to normal small intestine (calibrator). A matching pair is formed by mRNA from the cancer sample for a particular tissue and mRNA from the normal adjacent sample for that same tissue from the same individual.

TABLE 10

Relative Levels of CSG Pro110 Expression in Individual Samples

| Sample ID | Tissue | Cancer | Matching Normal Adjacent |
|---|---|---|---|
| Pro12B | Prostate 1 | 11.8 | 0.3 |
| Pro78XB | Prostate 2 | 14.3 | 6.3 |
| Pro101XB | Prostate 3 | 33.2 | 10.7 |
| Pro13XB | Prostate 4 | 0.3 | 0.4 |
| Pro23XB | Prostate 5 | 25.5 | 14.4 |
| Pro20XB | Prostate 6 | 43.3 | 4 |
| Pro34XB | Prostate 7 | 31.8 | 18.7 |
| Pro65XB | Prostate 8 | 26.9 | 3.4 |
| Pro69XB | Prostate 9 | 12.5 | 7 |
| Lng75XC | Lung 1 | 1.9 | 3 |
| Lng90X | Lung 2 | 5.5 | 0.5 |
| LngAC11 | Lung 3 | 9.3 | 9.7 |
| LngAC32 | Lung 4 | 11.2 | 2.2 |
| Lng47XQ | Lung 5 | 11.3 | 0.3 |
| Lng60XL | Lung 6 | 29.1 | 6.8 |
| Mam12B | Mammary Gland 1 | 19.8 | 0 |
| Mam603X | Mammary Gland 2 | 13.7 | 0 |
| Mam82XI | Mammary Gland 3 | 73.5 | 0 |
| MamA04 | Mammary Gland 4 | 0 | 24.6 |
| MamB011X | Mammary Gland 5 | 17.4 | 2 |
| MamC012 | Mammary Gland 6 | 0 | 12.8 |
| MamC034 | Mammary Gland 7 | 0 | 61 |
| Mam12X | Mammary Gland 8 | 14 | 2.2 |
| Mam59X | Mammary Gland 9 | 33 | 2.2 |
| MamA06X | Mammary Gland 10 | 16.4 | 0.8 |
| Liv15XA | Liver 1 | 1.7 | 0.6 |
| Liv42X | Liver 2 | 7.5 | 2.6 |
| Liv94XA | Liver 3 | 0.4 | 1.4 |
| ClnAS43 | Colon 1 | 52.9 | 1.4 |

TABLE 10-continued

Relative Levels of CSG Pro110 Expression in Individual Samples

| Sample ID | Tissue | Cancer | Matching Normal Adjacent |
|---|---|---|---|
| ClnAS45 | Colon 2 | 2.1 | 0.8 |
| ClnAS46 | Colon 3 | 39.8 | 3.7 |
| SmI21X | Small Intestine 1 | 0.9 | 0.1 |
| SmIH89 | Small Intestine 2 | 5.8 | 0.9 |

0 = Negative

The levels of mRNA expression in cancer samples and the isogenic normal adjacent tissue from the same individual were compared. This comparison provides an indication of specificity for the cancer (e.g. higher levels of mRNA expression in the cancer sample compared to the normal adjacent). Table 10 shows overexpression of Pro110 in 8 of the 9 primary prostate cancer tissues compared with their respective normal adjacent (except prostate 4). Thus, there was overexpression in 88.88% of the cancer prostate tissue as compared to the prostate matching samples tested (total of 9 prostate matching samples).

Although not tissue specific, Pro110 mRNA expression is upregulated in prostate cancer tissues. The mRNA overexpression in 88.88% of the primary prostate matching cancer samples tested is indicative of Pro110 being a diagnostic marker for prostate cancer. Pro110 also showed overexpression in several other cancers tested including small intestine, colon, liver, mammary and lung (see Table 10). Accordingly Pro110 may be a diagnostic marker for other types of cancer as well.

Expression of Clone ID 1857415; Gene ID 346880 (Pro113)

For the CSG Pro113, real-time quantitative PCR was performed using the following primers:

Forward Primer

5'-CGGGAACCTACCAGCCTATG-3'    (SEQ ID NO:31)

Reverse Primer

5'-CAGGCAACAGGGAGTCATGT-3'    (SEQ ID NO:32)

The absolute numbers depicted in Table 11 are relative levels of expression of the CSG Pro113 in 12 normal different tissues. All the values are compared to normal thymus (calibrator). These RNA samples are commercially available pools, originated by pooling samples of a particular tissue from different individuals.

TABLE 11

Relative Levels of CSG Pro113 Expression in Pooled Samples

| Tissue | NORMAL |
|---|---|
| Brain | 0.03 |
| Heart | 0 |
| Kidney | 0.01 |
| Liver | 0 |
| Lung | 0 |
| Mammary Gland | 0 |
| Muscle | 0.04 |
| Prostate | 489.44 |
| Small Intestine | 0.02 |

TABLE 11-continued

Relative Levels of CSG Pro113 Expression in Pooled Samples

| Tissue | NORMAL |
|---|---|
| Testis | 0.35 |
| Thymus | 1 |
| Uterus | 0.13 |

The relative levels of expression in Table 11 show that Pro113 mRNA expression is higher (489.44) in prostate compared with all the other normal tissues analyzed. Testis, with a relative expression level of 0.35, uterus (0.13), thymus (1.0), kidney (0.01) and brain (0.03) were among the other tissues expressing lower mRNA levels for Pro113These results establish that Pro113 mRNA expression is highly specific for prostate.

The absolute numbers in Table 11 were obtained analyzing pools of samples of a particular tissue from different individuals. They cannot be compared to the absolute numbers originated from RNA obtained from tissue samples of a single individual in Table 12.

The absolute numbers depicted in Table 12 are relative levels of expression of Pro113 in 78 pairs of matching and 25 unmatched tissue samples. All the values are compared to normal thymus (calibrator). A matching pair is formed by mRNA from the cancer sample for a particular tissue and mRNA from the normal adjacent sample for that same tissue from the same individual. In cancers (for example, ovary) where it was not possible to obtain normal adjacent samples from the same individual, samples from a different normal individual were analyzed.

TABLE 12

Relative Levels of CSG Pro113 Expression in Individual Samples

| Sample ID | Tissue | Cancer | Matched or Unmatched Normal Adjacent |
|---|---|---|---|
| Pro780B/781B | Prostate 1 | 375.58 | 446.29 |
| Pro1291B/1292B | Prostate 2 | 1060 | 31 |
| Pro139B96/140B96 | Prostate 3 | 41 | 32 |
| Pro209B96/210B96 | Prostate 4 | 505 | 255 |
| Pro1256B/1257B | Prostate 5 | 165.79 | 141.63 |
| Pro1293B/1294B | Prostate 6 | 1613.7 | 874.61 |
| Pro694B/695B | Prostate 7 | 458.6 | 142.21 |
| Pro1012B/1013B | Prostate 8 | 1520 | 864 |
| Pro1222B/1223B | Prostate 9 | 939 | 530 |
| Pro845B/846B | Prostate 10 | 1552.4 | 374.6 |
| Pro1094B/1095B | Prostate 11 | 278.37 | 135.89 |
| Pro650B/651B | Prostate 12 | 532.81 | 640.85 |
| Pro902B/903B | Prostate 13 | 609.05 | 415.86 |
| Pro916B/917B | Prostate 14 | 699.42 | 401.24 |
| Pro9821110A/110B | Prostate 15 | 156 | 487.8 |
| ProS9821326A/26B | Prostate 16 | 744.4 | 472.8 |
| Pro9407c215 | Prostate 17 | 1389.2 | |
| Pro9407c234 | Prostate 18 | 305.5 | |
| Pro9407c280A | Prostate 19 | 894.5 | |
| Pro9409C010R | Prostate 20 (prostatitis) | 269.7 | |
| Pro9404C120R | Prostate 21 (prostatitis) | 299.2 | |
| Pro1000258 | Prostate 22 (BPH) | 149.6 | |
| Pro4001263C | Prostate 23 (BPH) | 576 | |
| Pro4001267A | Prostate 24 (BPH) | 132.1 | |
| Pro9411C032 | Prostate 25 (BPH) | 118.2 | |
| Pro4001460Z | Prostate 26 (BPH) | 276.3 | |
| Pro4001271A | Prostate 27 (BPH) | 58.7 | |
| Kid1064D/65D | Kidney 1 | 0 | 0.1 |
| Kid1079D/1080D | Kidney 2 | 0.3 | 0.02 |
| Kid1097D/1098D | Kidney 3 | 35.14 | 0.32 |
| Kid1024D/1025D | Kidney 4 | 1.31 | 0 |
| Kid1183D/1184D | Kidney 5 | 24.79 | 0 |
| Kid1242D/1243D | Kidney 6 | 0 | 0 |
| Bld469K | Bladder 1 | | 2.88 |
| Bld467K/468K | Bladder 2 | 2.65 | |
| Bld327K/328K | Bladder 3 | 0 | 4.05 |
| Bld470K | Bladder 4 | | 1.64 |
| Bld665T/664T | Bladder 5 | 0.21 | 1.99 |
| Bld1496K/1497K | Bladder 6 | 13.55 | 1.14 |
| Bld1721K/1722K | Bladder 7 | 120.16 | 1.34 |
| Tst239X/240X | Testis 1 | 31.5 | 0.73 |
| TstS9820647A/47B | Testis 2 | 15.7 | 0 |
| TstS9820663A/663B | Testis 3 | 72 | 1.4 |
| SknS9821248A/248B | Skin 1 | 1.8 | 0.5 |
| SknS99448A/448B | Skin 2 | 251.6 | 0 |
| Skn99816A/816B | Skin 3 | 33 | 0.7 |
| Sto4004864A4/B4 | Stomach 1 | 14.12 | 0 |
| Sto4004509A3/B1 | Stomach 2 | 40.74 | 39 |
| SmI9807A212A/213A | Small Intestine 1 | 0.1 | 0 |
| SmI9802H008/R009 | Small Intestine 2 | 5.8 | 0.1 |
| Cln9608B012/B011 | Colon 1 | 4.5 | 0 |
| Cln9709c074ra/073ra | Colon 2 | 65.8 | 3.1 |
| Cln4004709A1/709B1 | Colon 3 | 1.1 | 0.9 |
| Cln9405C199/C200 | Colon 4 | 31.76 | 0.73 |
| Cln9707c004gb/006ga | Colon 5 | 90.26 | 0.96 |
| Cln96-09-B004/B003 | Colon 6 | 17.9 | 20.64 |
| Cln9612B006/B005 | Colon 7 | 17.56 | 0.3 |
| Cln9705F002D/F001C | Colon 8 | 21.39 | 0 |
| ClnCXGA | Colon 9 | 429.14 | 142.69 |
| Pan10343a | Pancreas 1 | 0 | 0 |
| Pan776P/777P | Pancreas 2 | 0 | 0.15 |
| Pan921O/922O | Pancreas 3 | 7.36 | 0 |
| Pan714L/715L | Pancreas 4 | 13.57 | 0.11 |
| Pan824P/825P | Pancreas 5 | 0 | 0 |
| Lng476Q/477Q | Lung 1 | 0 | 0 |
| Lng605L/606L | Lung 2 | 0 | 0.1 |
| Lng11145B/11145C | Lung 3 | 85.9 | 0 |
| Lng0008632A/32B | Lung 4 | 23.85 | 0 |
| Lng750C/751C | Lung 5 | 0.32 | 0.25 |
| Lng8890A/8890B | Lung 6 | 10.63 | 0 |
| Lng8926A/8926B | Lung 7 | 15.37 | 0 |
| Lng0010239A/39B | Lung 8 | 26.17 | 0 |
| Lng9502C109R/110R | Lung 9 | 0.68 | 0 |
| LngS9821944a/44b | Lung 10 | 0 | 0 |
| Mam00042D01/42N01 | Mammary Gland 1 | 8.5 | 0 |
| Mam59XC | Mammary Gland 2 | 61.07 | 0 |
| Mam9706A066G/67C | Mammary Gland 3 | 4.84 | 0 |
| Mam14153a1C | Mammary Gland 4 | 9.72 | 6.99 |
| Mam1620F/1621F | Mammary Gland 5 | 0.91 | 0 |
| Mam00014D05 | Mammary Gland 6 | 2.45 | 0 |
| End10479B/D | Endometrium 1 | 133.43 | 1.12 |
| End9705A125A/126A | Endometrium 2 | 0 | 0.39 |
| End9704C281A/282A | Endometrium 3 | 23.5 | 1.56 |
| End680o97/681o97 | Endometrium 4 | 88.89 | 79.02 |
| Utr1359O/1358O | Uterus 1 | 0.2 | 0 |
| Utr850U/851U | Uterus 2 | 0 | 0 |
| Utr1417O/1418O | Uterus 3 | 14 | 0.4 |
| Utr233U96/234U96 | Uterus 4 | 8.65 | 4.64 |
| CvxVNM00052D01/52N01 | Cervix 1 | 0.82 | 77.15 |
| CvxVNM00083D01/83N01 | Cervix 2 | 0.78 | 221.48 |
| CvxND00023D01/23N01 | Cervix 3 | 3.25 | 15.22 |
| Ovr1037O/1038O | Ovary 1 | 0.1 | 0 |
| Ovr1005O | Ovary 2 | 18.96 | |

TABLE 12-continued

Relative Levels of CSG Pro113 Expression in Individual Samples

| Sample ID | Tissue | Cancer | Matched or Unmatched Normal Adjacent |
|---|---|---|---|
| Ovr1028 | Ovary 3 | 0 | |
| Ovr14638A1C | Ovary 4 | 3.2 | |
| Ovr14603A1D | Ovary 5 | 882.3 | |
| Ovr7730 | Ovary 6 | 0 | |
| Ovr9702C018GA | Ovary 7 | | 0.15 |
| Ovr206I | Ovary 8 | | 0 |
| Ovr9702C020GA | Ovary 9 | | 0 |
| Ovr9702C025GA | Ovary 10 | | 0 |
| Ovr9701C035GA | Ovary 11 | | 0.07 |
| Ovr9701C050GB | Ovary 12 | | 0.58 |

0 = Negative

In the analysis of matching samples, the higher levels of expression were in prostate, showing a high degree of tissue specificity for prostate tissue. In addition to the higher expression levels in prostate cancer samples, Pro113 expression was found to be either induced (where not expressed in normal adjacent tissues) or somewhat upregulated in several other cancers. However, the relative expression and the fold increase in prostate cancer samples far exceeds that in other cancer tissues and is highly significant.

Furthermore, the levels of mRNA expression in cancer samples and the isogenic normal adjacent tissue from the same individual were compared. This comparison provides an indication of specificity for the cancer (e.g. higher levels of mRNA expression in the cancer sample compared to the normal adjacent). Table 12 shows overexpression of Pro113 in 13 out of 16 primary prostate cancer tissues compared with their respective normal adjacent (prostate samples 2, 3, 4, 5, 6 7, 8, 9, 10, 11, 13, 14, 16). Thus, there was overexpression in the cancer tissue for 81.25% of the prostate matching samples tested. The median for the level of expression in prostate cancer tissue samples is 609, whereas the median for all other cancers is only 7.93, with the exception of one colon sample, colon 9, whose expression was similar to that found in prostate cancer tissues.

Altogether, the high level of tissue specificity, plus the mRNA overexpression in 81.25% of the primary prostate matching samples tested are indicative of Pro113 being a diagnostic marker for prostate cancer. Expression was also found to be higher in other cancer tissues compared with their respective normal adjacent tissues (kidney, bladder, testis, skin, stomach, small intestine, colon, pancreas, lung, mammary, endometrium, uterus, and ovary) thus indicating Pro113 to be a pan cancer marker.

Expression of Clone ID 1810463H1 (Pro114)

For the CSG Pro114, real-time quantitative PCR was performed using the following primers:

Forward Primer

5'-TGGGCATCTGGGTGTCAA-3'          (SEQ ID NO:33)

Reverse Primer

5'-CGGCTGCGATGAGGAAGTA-3'         (SEQ ID NO:34)

The absolute numbers depicted in Table 13 are relative levels of expression of the CSG Pro114 in 12 normal different tissues. All the values are compared to normal muscle (calibrator). These RNA samples are commercially available pools, originated by pooling samples of a particular tissue from different individuals.

TABLE 13

Relative Levels of CSG Pro114 Expression in Pooled Samples

| Tissue | NORMAL |
|---|---|
| Brain | 9.7 |
| Heart | 0.7 |
| Kidney | 414.4 |
| Liver | 4 |
| Lung | 882.2 |
| Mammary | 44 |
| Muscle | 1 |
| Prostate | 1951 |
| Small Intestine | 22 |
| Testis | 367.1 |
| Thymus | 25.8 |
| Uterus | 139.6 |

The relative levels of expression in Table 13 show that Pro114 mRNA expression is higher (1951) in prostate compared with all the other normal tissues analyzed. Lung, with a relative expression level of 882.2, kidney 414.4, testis 367.1 and uterus 139.6, are the other tissues expressing higher levels of mRNA for Pro114. These results establish Pro114 mRNA expression to be more specific for prostate than other tissues examined.

The high level of tissue specificity is indicative of Pro114 being a diagnostic marker for diseases of the prostate, especially cancer.

Expression of Clone ID zr65g11 (Pro118)

For the CSG Pro118, real-time quantitative PCR was performed using the following primers:

Forward Primer

5'-GCCCATCTCCTGCTTCTTTAGT-3'      (SEQ ID NO:35)

Reverse Primer

5'-CGTGGAGATGGCTCTGATGTA-3'       (SEQ ID NO:36)

The absolute numbers depicted in Table 14 are relative levels of expression of the CSG Pro118 in 12 normal different tissues. All the values are compared to normal kidney (calibrator). These RNA samples are commercially available pools, originated by pooling samples of a particular tissue from different individuals.

TABLE 14

Relative Levels of CSG Pro118 Expression in Pooled Samples

| Tissue | NORMAL |
|---|---|
| Colon | 0.87 |
| Endometrium | 19282 |
| Kidney | 1 |
| Liver | 0 |
| Ovary | 86.21 |
| Pancreas | 0 |
| Prostate | 962.1 |
| Small Intestine | 0 |
| Spleen | 0.75 |
| Stomach | 0.54 |
| Testis | 343.7 |
| Uterus | 1064 |

The relative levels of expression in Table 14 show that Pro118 mRNA expression is the $3^{rd}$ highest in prostate (962.1) next to endometrium (19282) and uterus (1064), which are female-specific tissues. Testis, with a relative expression level of 343.7 is the only other male tissue expressing moderate levels of mRNA for Pro118. These results establish Pro118 mRNA expression to be highly specific for reproductive tissues including the prostate.

The absolute numbers in Table 14 were obtained analyzing pools of samples of a particular tissue from different individuals. They cannot be compared to the absolute numbers originated from RNA obtained from tissue samples of a single individual in Table 15.

The absolute numbers depicted in Table 15 are relative levels of expression of Pro118 in 59 pairs of matching and 21 unmatched samples. All the values are compared to normal kidney (calibrator). A matching pair is formed by mRNA from the cancer sample for a particular tissue and mRNA from the normal adjacent sample for that same tissue from the same individual.

TABLE 15

Relative Levels of CSG Pro118 Expression in Individual Samples

| Sample ID | Tissue | Cancer | Matching Normal Adjacent |
|---|---|---|---|
| Pro12B | Prostate 1 | 41700.7 | 22242.83 |
| ProC234 | Prostate 2 | 40087 | |
| Pro78XB | Prostate 3 | 4075.6 | 7066.7 |
| Pro109XB | Prostate 4 | 334.4 | 777.2 |
| Pro84XB | Prostate 5 | 11684 | 58290 |
| Pro101XB | Prostate 6 | 21474.13 | 100720.8 |
| Pro91X | Prostate 7 | 14849 | 33717 |
| Pro13XB | Prostate 8 | 202.57 | 146.91 |
| ProC215 | Prostate 9 | 73243 | |
| Pro125XB | Prostate 10 | 629.6 | 521.4 |
| Pro23B | Prostate 11 | 157532.6 | 110654.4 |
| Pro90XB | Prostate 12 | 2317 | 64134 |
| ProC280 | Prostate 13 | 42020 | |
| Pro20XB | Prostate 14 | 2909.31 | |
| Pro34B | Prostate 15 | 29610 | 23264 |
| Pro110 | Prostate 16 | 13354 | 30991 |
| Pro65XB | Prostate 17 | 10126 | 11270 |
| Pro69XB | Prostate 18 | | 2671.42 |
| Pro326 | Prostate 19 | 9962.3 | 19231 |
| Pro10R | Prostate 20 (prostatitis) | 27355 | |
| Pro20R | Prostate 21 (prostatitis) | 21081 | |
| Pro258 | Prostate 22 (BPH) | 79916.32 | |
| Pro263C | Prostate 23 (BPH) | 108924.5 | |
| Pro267A | Prostate 24 (BPH) | 92910.22 | |
| Pro271A | Prostate 25 (BPH) | 57004.4 | |
| Pro460Z | Prostate 26 (BPH) | 57449.23 | |
| ProC032 | Prostate 27 (BPH) | 45781.44 | |
| Kid106XD | Kidney 1 | 3.08 | 217.36 |
| Kid107XD | Kidney 2 | 0 | 38.36 |
| Kid109XD | Kidney 3 | 0 | 123.5 |
| Kid10XD | Kidney 4 | 17.69 | 67.8 |
| Kid11XD | Kidney 5 | 16.74 | 360.8 |
| Kid124D | Kidney 6 | 0 | 167.4 |
| Bld32XK | Bladder 1 | 0 | 0 |
| Bld47K | Bladder 2 | | 36.38 |
| Bld66X | Bladder 3 | 0 | 4.52 |
| BldTR14 | Bladder 4 | 0 | 12.17 |
| BldTR17 | Bladder 5 | 0 | 0 |
| Bld46XK | Bladder 6 | 16.5 | 0 |
| Tst39X | Testis 1 | 116.6 | 24.35 |
| Tst647T | Testis 2 | 856.16 | 43.5 |
| StoAC44 | Stomach 1 | 0 | 0 |
| StoAC93 | Stomach 2 | 0 | 0 |
| SmI21XA | Small Intestine 1 | 68.45 | 0 |
| SmIH89 | Small Intestine 2 | 0 | 0 |
| ClnAC19 | Colon 1 | 149 | 21.33 |
| ClnAS12 | Colon 2 | 0 | 0 |
| ClnB34 | Colon 3 | 0 | 0 |
| ClnB56 | Colon 4 | 13.04 | 5.22 |
| ClnAS43 | Colon 5 | 0 | 0 |
| Lng47XQ | Lung 1 | 0 | 0 |
| Lng60XL | Lung 2 | 0 | 0 |

TABLE 15-continued

Relative Levels of CSG Pro118 Expression in Individual Samples

| Sample ID | Tissue | Cancer | Matching Normal Adjacent |
|---|---|---|---|
| Lng75XC | Lung 3 | 0 | 3.38 |
| Lng90X | Lung 4 | 0 | 0 |
| LngBR26 | Lung 5 | 0 | 26.82 |
| Pan10343 | Pancreas 1 | 50.47 | 0 |
| Pan77X | Pancreas 2 | 281.1 | 0 |
| Pan92X | Pancreas 3 | 18.41 | 0 |
| Pan71XL | Pancreas 4 | 0 | 0 |
| Pan82XP | Pancreas 5 | 0 | 0 |
| PanC044 | Pancreas 6 | 0 | 0 |
| Mam12X | Mammary Gland 1 | 0 | 0 |
| Mam162X | Mammary Gland 2 | 0 | 0 |
| Mam42DN | Mammary Gland 3 | 0 | 0 |
| MamS127 | Mammary Gland 4 | 12.58 | 0 |
| Mam14DN | Mammary Gland 5 | 0 | 0 |
| End28XA | Endometrium 1 | 331.9 | 1824 |
| End3AX | Endometrium 2 | 27825 | 65839 |
| End4XA | Endometrium 3 | 10.3 | 15935 |
| Utr141O | Uterus 1 | 18885 | 18116 |
| Utr23XU | Uterus 2 | 3358 | 7674 |
| CvxKS52 | Cervix 1 | 0 | 0 |
| CvxKS83 | Cervix 2 | 0 | 0 |
| Ovr1005O | Ovary 1 | 72.86 | |
| Ovr1028 | Ovary 2 | 0 | |
| Ovr638A | Ovary 3 | 0 | |
| Ovr63A | Ovary 4 | 90.88 | |
| Ovr7730 | Ovary 5 | 1.21 | |
| Ovr1040O | Ovary 6 | 5.08 | |
| Ovr105O | ovary 7 | 0 | |
| Ovr1118 | Ovary 8 | 7.41 | |
| Ovr103X | Ovary 9 | | 32.78 |
| Ovr20GA | Ovary 10 | | 0 |
| Ovr25GA | Ovary 11 | | 1173.83 |
| Ovr35GA | Ovary 12 | | 313.4 |
| Ovr50GB | Ovary 13 | | 823.1 |
| Ovr18GA | Ovary 14 | | 40.6 |
| Ovr206I | Ovary 15 | | 1264 |
| Ovr230A | Ovary 16 | | 1285 |

0 = Negative

In the analysis of matching samples, the higher levels of expression were in prostate, endometrium, testis, and ovary showing a high degree of tissue specificity for reproductive tissues. These results confirmed the tissue specificity results obtained with the panel of normal pooled samples (Table 14).

Furthermore, the levels of mRNA expression in cancer samples and the isogenic normal adjacent tissue from the same individual were compared. This comparison provides an indication of specificity for the cancer (e.g. higher levels of mRNA expression in the cancer sample compared to the normal adjacent). Table 15 shows overexpression of Pro118 in 5 out of 14 primary prostate cancer tissues (prostate samples 1, 8, 10, 11, 15) compared with their respective normal adjacent. Thus, there was overexpression in the cancer tissue for 35.71% of the prostate matching samples tested (total of 14 prostate matching samples). Expression of Pro118 was similarly higher in 3 unmatched cancer tissues (prostate samples 9, 13, 14), 2 prostatitis (prostate samples 20, 21), and 6 benign hyperplasia tissues (prostate samples 22 through 27).

Altogether, the high level of tissue specificity, plus the mRNA overexpression in 35.71% of the primary prostate matching samples tested are indicative of Pro118 being a diagnostic marker for prostate cancer.

What is claimed is:

1. A method for diagnosing the presence of prostate cancer in a patient comprising:
   (a) determining the level of SEQ ID NO: 7 or 8 in prostate cells, tissues or in blood, plasma, serum or urine from a patient; and
   b) comparing the determined level of SEQ ID NO: 7 or 8 with the level of SEQ ID NO: 7 or 8 in prostate cells, or tissues or blood, plasma, serum or urine from a normal human control, wherein an increase in the determined level of SEQ ID NO: 7 or 8 in said patient versus normal human control is associated with the presence of prostate cancer.

2. The method of claim 1 wherein the level of SEQ ID NO: 7 is determined.

3. The method of claim 1 wherein the level of SEQ ID NO: 8 is determined.

4. The method of claim 1 wherein the level of SEQ ID NO: 7 or 8 is determined in prostate cells.

5. The method of claim 1 wherein the level of SEQ ID NO: 7 or 8 is determined in prostate tissue.

6. The method of claim 1 wherein the level of SEQ ID NO: 7 or 8 is determined is determined in blood.

7. The method of claim 1 wherein the level of SEQ ID NO: 7 or 8 is determined in plasma.

8. The method of claim 1 wherein the level of SEQ ID NO: 7 or 8 is determined in serum.

9. The method of claim 1 wherein the level of SEQ ID NO: 7 or 8 is determined. in urine.

* * * * *

SEQUENCE LISTING

<160> NUMBER OF SEQ ID NOS: 36

<210> SEQ ID NO 1
<211> LENGTH: 188
<212> TYPE: DNA
<213> ORGANISM: Homo sapien

<400> SEQUENCE: 1

| ggtaaacacc tgcttttatc atcagaacaa agaggctgtg tcccctgccc tatgaggtcc | 60 |
| atttctgaga gttgtggcta atgggcaaga aggttgggc tttagagatt tgggataaag | 120 |
| atatcaaaca ccagaaaggt agaaagaagt gatcagatta gggttactta ggtgatgata | 180 |
| tgaactct | 188 |

<210> SEQ ID NO 2
<211> LENGTH: 9819
<212> TYPE: DNA
<213> ORGANISM: Homo sapiens

<400> SEQUENCE: 2

| cagctggggt ctacccaggt ccatgtcttg gacatgttga gagtttttct ggaaggcagg | 60 |
| gatacagtgt ggtccaaaaa cacacaaatg cccctactgg cccagggggtt gtcacaatag | 120 |
| actggaaggg tgacacatcc caggcgcttg ccacccatca cacgcacctc ctacccactg | 180 |
| gcatccttcc accccaggca cacacaaagc ctcagtccag agatcaactc tggactcagc | 240 |
| tctgaattg catatcctgt gtgtagattc attcttcata acctctgccc agcctagctt | 300 |
| gtgtatcatt ttttttctc tattagggga ggagcccgtc ctggcactcc cattggcctg | 360 |
| tagattcacc tccctgggc agggcccag gacccaggat aatatctgtg cctcctgccc | 420 |
| agaaccctcc aagcagacac aatggtaaga atggtgcctg tcctgctgtc tctgctgctg | 480 |
| cttctgggtc ctgctgtccc ccaggagaac caagatggtg agtggggaaa gcaagggatg | 540 |
| ggtgctggag aggactggaa ggaggtgagg aacaggacat gtggctggga gacaggctgg | 600 |
| atgcagctgg gatacctg catacggcag gaatgggtgc ccaaggctgt caactccctc | 660 |
| agctcacaca cttccaggag cattcaggga gcctctgcgc tggcccgaaa taagaccttc | 720 |
| aggaatctga atctaaaacc cctagtttac agtgaaaaca aagactccaa agaccaagcg | 780 |
| acctgcttgg ggtagacagt caggacggag taggaaccat atgcctggag ctgcttctgc | 840 |
| tcctgttcct tccctccttc cgatggctgg gtacacctgc ctgacgctga ggaaaagaga | 900 |
| gagcagcccc aagggggaaag tgggaaggca ggttggctgg agggatggtg ctagaaggaa | 960 |
| acccgtgccc aaatcccaca ctcagacacc actgcagtgg gtctggaagg cgagtggctg | 1020 |
| gaagagaaga gagtgggagc tccgggagat caagagtcac tcctaggata agggaaggag | 1080 |
| gctgtttgtg gcatgagaat gtgcaggata aagcatggaa agcgaatggc ttctcagttg | 1140 |
| tgtgagttta aaattcatga catttacaaa ttgtcagaaa aggtgttata tgtttgttat | 1200 |
| ataacaatca ctttgaatg ttaatctgat tctgtgccaa aatctgaatt actcaggggtt | 1260 |
| ctccagagaa acagaactaa taggtggtac acatatacat atatatgtac gtacacatac | 1320 |
| atacatacac tgtatacaca tggatacaca cacacatagg aagagattta catatatgta | 1380 |
| tacaaaagag agagagagta gagatttatt ttaagaaatt gactcacact attgggagga | 1440 |
| gtaacaagtc ctaaatcttc agagccggcc agcaggctgg agacccaggg aagagttgat | 1500 |
| gtcttagtct tgattccaag ggcagactgt aggcagaatt cttttcctctt taggggacat | 1560 |

```
ctgaggctttttctcttaag gccttcaact gattggatga agcccaccac tatggagagt    1620
aatccacttt actcaaggtc tactgatttt tttgtaaatt aaaaaaaaaa ctgtgggtgc    1680
atagtatgtg tatatattta tggggtacat gagaggtttt gattcaggca tgcaatgtga    1740
aataatcaca tcatcaaaaa tgaggtatcc atcccttcaa gcttttatcg tttgtgttac    1800
agacaatcca attatacttt tttggttatt ttagtttta aaagtatttg attatttatt    1860
tatttattta ttttttgagac agagtctcac tctgtcaccc aggcaggagt gcagtggcat    1920
gatctcggct cactgcaacc tccgcctccc aggttcaagc aattttcctg cctcagtctc    1980
ctgagtagct aggactacag gcacctgcca ccacacctgg ctaattttt tgtatttta    2040 gtagagacgg tttcatcatg ttggccaggc tagtcttgat atcctgacct cgtgatctgc    2100
ccgccttggt ctcccaaagt gccgggatta caggtgtcag caactgcgcc tggcctctct    2160
tttggttatt taaagtgta caattaaatt atgattatta ttattattt tgagatggat    2220 tcttgttctg tcacccaggc tggagtgcag tggcgtgatc ttggcttact gcaaacctcc    2280
gcctgttggg ttcaagcaat tatcttgcct cgggtgtaca ctgccacaca cggctaactt    2340
atgtattttt aatagagata gggtttcacc atgttggcta actggtctt gacctcttga    2400 cctcaagtga tccactcact tcagcctccc agagtgctgg aattacaggc acgagccacc    2460
acacctggcc ccagttaaat tattattgac tatagtcacc ctgttgtgct atcaaatagt    2520
aggtcttatt cattcttctt tttttttttt tttttgtgac agagttgccc aggctggaat    2580
gcagtggtgc aatcttggct cactgcaacc tctgcctccc gggcttaagc gattctcctg    2640
cctcagcctt ctgagtcgct gggactacag gtgtgtgcca ccacgcccgg ctaatttatg    2700
tatttttagt agagatgggg tttcaccatg ttggccaggc tggtttcgaa ctcctgacct    2760
caagtgaccc acctgcctca gcttcccaaa gtgttggaat tacaggcatg agccaccaca    2820
cctggcccca gttaaattat tattcactgg agtcactttg ttgtgctatc aaatagtttt    2880
ctaactattt ttttgtacc cattaaccac cctcccaatt tcccccaac cctgccacta    2940 cccttcccag ccttttggtaa ccatccttct actctctatg tccatgaatt caattgtagg    3000
gtctactgat ttaaaggcta atcacattta gacactcagg agcaagaata atttagtaa    3060 ttgaactagg attctgccat atgacctcca acatcattag cacctgtgta aattgtatca    3120
taaaataatt atggaactat tatggaaatg tccctctctc ccagatccca ccttgtacca    3180
aaatgcaagg tacaaccccg ggaattctga gctccatcct agtcttaccc tgtgctaatt    3240
cagtctgggt catttcttga atttctggt aaattctcct ttctacccttt tctaactata    3300 tgtatttgtc aggttaagct agaagtgtta atttttttt ttttgagat ggagccttgc    3360 tttgtcacct aggctgaagt gcagtggcat gatctcagct cactgcaagc tccgcctccc    3420
gggttcatgc cattctcctg cctcagcctc ctgagtagct gggactacag gcacccgcca    3480
ccatgcttgg ctaatttttt gaattcttag tagagacggg tttcaccat gttagccagg    3540 atggtctcga tctcctgacc tcgtgatcca cccgcctcgg cccctaaag tgctgggatt    3600 acaggcgtga gccactgagc ccggacgaaa tgttaatttg ttttttttga gacggagtct    3660
cactctgtca tccaagctgg agtgcagtgg catgatcttg gcttgttgca acctctgcct    3720
ctctggttca agtgattttc ctgcctcagc ctccagcatg actgggatta caggcccgca    3780
ccaccatgcc cagctaattt ttgtatttt taatagagat ggggtttcac catgttggcc    3840
aggctggtct tcaactcctg atctcaagta atctgcctgc cttggcctcc caaagtcctg    3900
```

-continued

```
ggattacagg catgagccac ggagcccagc ctagaaatgt taatttctaa cgcatgtcag    3960
attccatgca cactgggcaa ggttccattc ctccatgggg tgactcaggg atccaggcca    4020
attgcatatt gagactcttt catattatcc tgtggccttc aaagtcgtca cctctaggga    4080
tgagaaacaa aagggaaagc cagctggtag ggtcttggac aagaagaaag acatcacttc    4140
tgctcacatt ctcttttgac aaaactcagt cacatggtcc caatatatct tcgaggtggc    4200
tgagtaatgt tatcttccta tgtgtcaagc agaggaaata atgtagtgaa gacacaggat    4260
ggtctctgaa atatcatctc aggcatgaaa gtagagcata ttcacttgag tgagcctcca    4320
gtggtgtgaa gttgatggca ggagaaagag ctggggaaga aaaggccagt ggcaggtctc    4380
ccctcctagc cctatgcagc cccacagtgg gacccttgca tggacctcaa ccatcagaat    4440
cttttctttt gcaggtcgtt actctctgac ctatatctac actgggctgt ccaagcatgt    4500
tgaagacgtc cccgcgtttc aggcccttgg ctcactcaat gacctccagt tctttagata    4560
caacagtaaa gacaggaagt ctcagcccat gggactctgg agacaggtgg aaggaatgga    4620
ggattggaag caggacagcc aacttcagaa ggccagggag gacatcttta tggagaccct    4680
gaaagacatt gtggagtatt acaacgacag taacggtcag tgaataacag accacagggg    4740
tggaaggtct aacccaagag gcagccccc cagtgtgagt ggcaagggat cagcaggatg    4800
gaaatagtcc caatcccagg ggaagaacag gagacacagc agaaacacag acatgtccgc    4860
atcccaccca ccccacagca caggtgctcc ccgcttcccc atcaattgcc ccatcctcat    4920
cccaggcctc aggtcacaca ggaagtgatg gcagagtcac ttcctatcca ggcacctatg    4980
acctctcacc tccacacccc acccatcgga ggctgatacc cccgtgagaa ggcatcagac    5040
tcacccctgt ccagggaggt tgcctggaga gtgagccact ctcaaagtca ctcagacctg    5100
ggctcacctg gtggttctgc cagtcctagc tgttgacagt gaaacgttcc caaaatatct    5160
ggttgaaatc tgcaaacatt ggagcactga gacctacctc caaacaagtc tgtaatattt    5220
aactatgtct gttctatgaa ggatgtcaca gtctgtcctg atctcccttg cagctccatc    5280
acctagcaca gggtacagcc aatattggct caattgaaat ttgtggaatc cacagagaaa    5340
agcacccggc acacaccgta gcccatgctg ggggctcagg aagtgctgga ttcaaaactg    5400
tgggctgtta gagttccttg gagccctaaa gttcctcctt accatacgat gcagacccag    5460
gaagggccac ctgcgctatg gtcagaggag ctggtggcag agcccgtgca gagatggtcc    5520
ctgtgccccc ggcccagtgc tctttctcct aaaccacact gccagcccca aggcagccaa    5580
cctcaggtct ggtgaactgc tggtgttaaa ttatcataga gtgggtgtca aaagatgggc    5640
tactaagtac aaaaatgccc aaggtgctac atgggatctg aagattttca aaaggaggca    5700
agaaagagat aggcagatgt ttcaaggatg tggggtgggg gaggtcttgg taaggaaaat    5760
ggcccaggct gtgtgtcagc aataggagag gaggggcac aggtgatcag aaaagacact    5820
gggggaagca ttgatggaca ggaatagaaa tggcaaagtg gataattaag aggaaggagg    5880
atgaggagat gaacacaggg tattagaaaa taatagaagg cagggcttgg tggctcactc    5940
ttgtaatccc agcactttgg gaggctgagg caggcagatc acctaaggtc aggagttcga    6000
gaccagcccg gccaacatgg tgaaaccctg tctctactaa taatacaaaa atagcctggc    6060
atggtggcac acgtctgtgg tcccagctac tcaggaggct gaggcaggag aattgcttga    6120
acccaggagg cagaggttac agtggccaaa atcctaccat tgcactacag cctgggtgac    6180
aagagtgaaa cgttgtctaa aaacaaaaaa caaaaaacaa aaaaggaaa taatagtagc    6240 tgacatttac tgagcactta ctttgtgcca ggcccatcta tgagcatata taatgctcag    6300
```

-continued

```
aatagccccc taaaacagtg ctcttggcat tgccatttca gaggtgagga aatagaggca    6360
cagggagttg agtggctcca gttcaggcaa cacaccaggt gggggtgggg ggctggggag    6420
agacctggga cgtgagccca gacagcttga gagctttcag agtctatgcc aacagcacca    6480
accagtgctg ggtaaacacc tgcttttatc atcagaacaa agaggctgtg tccctgccc     6540 tatgaggtcc atttctgaga gttgtggcta atgggcaaga aggttgggc tttagagatt     6600 tgggataaag atatcaaaca ccagaaaggt agaagaagt gatcagatta ggttactta      6660 ggtgatgata tgaactcttc ctagaactga gagaaaaga gagccttcct ttactcatat     6720
gaaatcacaa ataatttcta tccaatttgg aagtacactt tggtgtagtt gtgacagctt    6780
cctcaggact cagcataaat tcaaacaaat aattgtcctt agaagagatg ctatagaaga    6840
gatagaaata tattcatatt ctgtagcttt ttttttttg agatggagtt ttgctcttgt     6900
cacccaagct ggagtgcagt gatgcaatct cagctcactg caaactttgc ctcctgggtt    6960
caagggattc tcctgcctca gcctcccgat aactgggact acaggctaca ggcatgtgtc    7020
actactcctg gttaattttt tttttttttt tttaagactg agtcttgctc tgtctttcag    7080
gctgatgtac aatggctcca tctcggctca ctacaacttc tgtcccccag gttcaagcga    7140
ttctcctgcc tcagcctcat gagtagctgg gattacaggc atgtgccagc acacccagca    7200 aattttgta tttttagtag agatgaggtc ttaccatgtt ggccaggctg gtctcaaact     7260
cctgacctca ggtgatcctt tggcctcagc ctccctaact gctgggatta caggcatgag    7320
ccactgcgtc cagcctaatt ttatattttt ggtagagatg gggtttcacc atattggcca    7380
ggctggtctc gaactcatga cctaaggtga tccatcctcc tcagcctctc aaagtgctgg    7440
gattacaagt gtgagccact gggcctggtg cttttttttt tttttttttt tttttttttt    7500
tgagataggg tctcactctg tcacccaggc tgaaatgcag tagtgtgatt ttggctcatt    7560
gcagccttga cttcccaggc tgaagtgatc ctcccacctc agcctcctga gtagctgggg    7620
ctacaggcat gcaccaccat gctgcgctaa ttttttatatt ttttgtagtg gtgggatttc    7680
gccatatcac cctggctggt ctggaacccc tgggctcaag cgatccactc gcttcagctt    7740
ctcaaagtgc tgggattaca ggcatgagcc acagcgccca ggctgtagct ctcttaagga    7800
ggaacatatc tcatctgaga caaacctgaa atgccaaacc aaactgagtt agcccctctc    7860
tgtctgttgt atatattgga gtaataacct atttgtcttg ataaagggat tgcatgcttg    7920
aattgcaaaa acctttattt cttttgggtt gcccaatgtg caagactaag agttattttg    7980
ataaatttct caccaggctg actgtctctc tgtggggtcg ggggagtttt cagggtctca    8040
cgtattgcag ggaaggtttg gttgtgagat cgagaataac agaagcagcg gagcattctg    8100
gaaatattac tatgatggaa aggactacat tgaattcaac aaagaaatcc cagcctgggt    8160 cccccttcgac ccagcagccc agataaccaa gcagaagtgg gaggcagaac cagtctacgt    8220
gcagcgggcc aaggcttacc tggaggagga gtgccctgcg actctgcgga aatacctgaa    8280
atacagcaaa aatatcctgg accggcaagg tactcactgc ttcctgctcc ccagtactga    8340
gcccagaata aaagacgatc tcaggctagg agctcaggca acatcttagt ccggtctcat    8400
ctgttcctgg atgtccctca gacccccagc tttcatcttt taggatttat tccttccctg    8460
ggataatata atttgtggtc caaaagaac atcatcaaaa tttcaggcag aatgggccag    8520
gaaggccatt ctttcttgat gagtgtcccc aaatcatctc caattaacag acaaggagct    8580
tgaggttagg gaggtgaggg taacactgtc tgtaagaggc agagctggga ctcaaattcc    8640
```

```
agatttcaga ttccaaatcc catcgttttt tatctctaca atgatgcctc ccatctgggt    8700
ggtggagaga agggaggcgt gtaaaagtca gccccagaag gacaagagca agccagtgtg    8760
agcggaattg atggctgcaa gctgagactt ggattggaga cgtagtgaga ctcaggattg    8820
tgcagtgctg cagggaagtg gttgctggat agaggcatgg gctgaaccaa gcagctggac    8880
tgagactggg ggacagaact ccaaagccca ctgagatgtg ggaaaacatg gagaagcaca    8940
cggagcattc acaacttatt gccgtcagag tcaatacatg ggtgaggtgg ggattgggca    9000
agagggaaag cgtcagcctt ccctgatatt ctggaaagtc tcccggggct ggggtgggc    9060 aggtacagag cttcgagctc tgctgatcgc tgacatccag gggtgggggt aggaagagac    9120
ctgggccggg agaagtccac ctcaagcctg cagtgtcaca ctctatccct ccacagatcc    9180
tccctctgtg gtggtcacca gccaccaggc cccaggagaa aagaagaaac tgaagtgcct    9240
ggcctacgac ttctacccag ggaaaattga tgtgcactgg actcgggccg gcgaggtgca    9300
ggagcctgag ttacggggag atgttcttca caatggaaat ggcacttacc agtcctgggt    9360
ggtggtggca gtgccccgc aggacacagc cccctactcc tgccacgtgc agcacagcag    9420
cctggcccag cccctcgtgg tgccctggga ggccagctag gaagcaaggg ttggaggcaa    9480
tgtgggatct cagacccagt agctgccctt cctgcctgat gtgggagctg aaccacagaa    9540
atcacagtca atggatccac aaggcctgag gagcagtgtg gggggacaga caggaggtgg    9600
atttggagac cgaagactgg gatgcctgtc ttgagtagac ttggacccaa aaaatcatct    9660
caccttgagc ccaccccac cccattgtct aatctgtaga agctaataaa taatcatccc    9720
tccttgccta gcataacaga gaatccttttt tttaacggtg atgcgctgta gaaatgtgac    9780
tagattttct cattggttct gccctcaagc actgaattc                          9819

<210> SEQ ID NO 3
<211> LENGTH: 250
<212> TYPE: DNA
<213> ORGANISM: Homo sapiens

<400> SEQUENCE: 3
cgcccctgcg ccgccgagcc agctgccaga atgccgaact ggggaggagg caagaaatgt     60
ggggtgtgtc agaagacggt ttactttgcc gaagaggttc agtgcgaagg caacagcttc    120
cataaatcct gcttcctgtg catggtctgc aagaagaatc tggacagtac cactgtggcc    180
gtgcatggtg aggagattta ctgcaagtcc tgctacggca agaagtatgg gcccaaaggc    240
tatggctacg                                                          250

<210> SEQ ID NO 4
<211> LENGTH: 1900
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n=a, c, g or t
<220> FEATURE:
<221> NAME/KEY: misc_feature
<222> LOCATION: (18)..(18)
<223> OTHER INFORMATION: n=a, c, g or t
<220> FEATURE:
<221> NAME/KEY: misc_feature
<222> LOCATION: (20)..(20)
<223> OTHER INFORMATION: n=a, c, g or t
<220> FEATURE:
<221> NAME/KEY: misc_feature
<222> LOCATION: (1887)..(1887)
<223> OTHER INFORMATION: n=a, c, g or t
```

<220> FEATURE:
<221> NAME/KEY: misc_feature
<222> LOCATION: (1894)..(1894)
<223> OTHER INFORMATION: n=a, c, g or t

<400> SEQUENCE: 4

| | | | | | |
|---|---|---|---|---|---|
| acgccttccg | cggagnanan | caaaacggcg | cgcaggccgg | gcgcacccag | ccgccacttc | 60 |
| cgagagcgcc | tgccgcccct | ggcgccgccg | agccagctgc | cagaatgccg | aactggggag | 120 |
| gaggcaagaa | atgtggggtg | tgtcaagaag | acggtttact | ttgccgaaga | ggttcagtgc | 180 |
| gaaggcaaca | gcttccataa | atcctgcttc | ctgtgcatgg | tctgcaagaa | gaatctggac | 240 |
| agtaccactg | tgggccgtgc | atggtgagga | gatttactgg | caagtccctg | ctacggcaag | 300 |
| aagtatgggc | ccaaaggcta | tggctacggg | ccagggcgca | ggcaccctca | gcactgacaa | 360 |
| gggggagtcg | ctgggtatca | agcacgagga | agccctggg | ccacaggccc | accaccaacc | 420 |
| ccaatggcat | ccaaatttgc | ccagaagatt | ggtggctccg | agcgctgccc | ccgatgcagc | 480 |
| caggcagtct | atgctgcgga | gaaggtgatt | ggtgctggga | agtcctggca | taaggcctgc | 540 |
| tttcgatgtg | ccagtgtgg | caaaggcctt | gagtcaacca | ccctgggcag | acaaggatgg | 600 |
| cgagatttac | tgcaaaggat | gttatgctaa | aaacttcggg | cccaagggct | ttggttttgg | 660 |
| gcaaggagct | ggggccttgg | tccactctga | gtgaggccac | catcacccac | cacaccctgc | 720 |
| ccactcctgc | gcttttcatc | gccattccat | tcccagcagc | tttggagacc | tccaggatta | 780 |
| tttctctgtc | agccctgcca | catatcacta | atgacttgaa | cttgggcatc | tggctccctt | 840 |
| tggtttgggg | gtctgcctga | gtcccacccc | cactaaaggg | ctcccaggc | ctgggatctg | 900 |
| acaccatcac | cagtaggaga | cctcagtgtt | ttgggtctag | gtgagagcag | gcccctctcc | 960 |
| ccacacctcg | ccccacagag | ctctgttctt | agcctcctgt | gctgcgtgtc | catcatcagc | 1020 |
| tgaccaagac | acctgaggac | acatcttggc | acccagagga | gcagcagcaa | caggctggag | 1080 |
| ggagagggaa | gcaagaccaa | gatgaggagg | ggggaaggct | gggttttttg | gatctcagag | 1140 |
| attctcctct | gtgggaaaga | ggttgagctt | cctggtgtcc | ctcagagtaa | gcctgaggag | 1200 |
| tcccagctta | gggagttcac | tattggaggc | agagaggcat | gcaggcaggg | tcctaggagc | 1260 |
| ccctgcttct | ccaggcctct | tgcctttgag | tctttgtgga | atggatagcc | tcccactagg | 1320 |
| actgggagga | gaataaccca | ggtcttaagg | accccaaagt | caggatgttg | tttgatcttc | 1380 |
| tcaaacatct | agttccctgc | ttgatgggag | gatcctaatg | aaatacctga | aacatatatt | 1440 |
| ggcatttatc | aatggctcaa | atcttcattt | atctctggcc | ttaaccctgg | ctcctgaggc | 1500 |
| tgcggccagc | agagcccagg | ccagggctct | gttcttgcca | cacctgcttg | atcctcagat | 1560 |
| gtggagggag | gtaggcactg | cctcagtctt | catccaaaca | cctttccctt | tgccctgaga | 1620 |
| cctcagaatc | ttcccttaa | cccaagaccc | tgcctcttcc | actccaccct | tctccaggga | 1680 |
| cccttagatc | acatcactcc | accctgcca | ggcccaggt | taggaatagt | ggtgggagga | 1740 |
| agggaaagg | gctgggcctc | accgctccca | gcaactgaaa | ggacaacact | atctggagcc | 1800 |
| acccactgaa | agggctgcag | gcatgggctg | tacccaagct | gatttctcat | ctggtcaata | 1860 |
| aagctgttta | gaccagaaaa | aaaaaanaaa | aaanaaaagg | | | 1900 |

<210> SEQ ID NO 5
<211> LENGTH: 273
<212> TYPE: DNA
<213> ORGANISM: Homo sapiens

<400> SEQUENCE: 5

| gatgcatcaa aagagctgca agttctccac attgacttct tgaatcagga caacgccgtt | 60 |
| tctcaccaca catgggagtt ccaaacgagc agtcctgtgt tccggcgagg acaggtgttt | 120 |
| cacctgcggc tggtgctgaa ccagccccta caatcctacc accaactgaa actggaattc | 180 |
| agcacagggc cgaatcctag catcgccaaa cacaccctgg tggtgctcga cccgaggacg | 240 |
| ccctcagacc actacaactg gcaggcaacc ctt | 273 |

<210> SEQ ID NO 6
<211> LENGTH: 3021
<212> TYPE: DNA
<213> ORGANISM: Homo sapiens

<400> SEQUENCE: 6

| tgtggaagca ccaggcatca gagatagagt cttccctggc attgcaggag agaatctgaa | 60 |
| gggatgatgg atgcatcaaa agagctgcaa gttctccaca ttgacttctt gaatcaggac | 120 |
| aacgccgttt ctcaccacac atgggagttc caaacgagca gtcctgtgtt ccggcgagga | 180 |
| caggtgtttc acctgcggct ggtgctgaac cagcccctac aatcctacca ccaactgaaa | 240 |
| ctggaattca gcacagggcc gaatcctagc atcgccaaac acaccctggt ggtgctcgac | 300 |
| ccgaggacgc cctcagacca ctacaactgg caggcaaccc ttcaaaatga gtctggcaaa | 360 |
| gaggtcacag tggctgtcac cagttccccc aatgccatcc tgggcaagta ccaactaaac | 420 |
| gtgaaaactg gaaccacat ccttaagtct gaagaaaaca tcctatacct tctcttcaac | 480 |
| ccatggtgta aagaggacat ggttttcatg cctgatgagg acgagcgcaa agagtacatc | 540 |
| ctcaatgaca cgggctgcca ttacgtgggg gctgccagaa gtatcaaatg caaaccctgg | 600 |
| aactttggtc agtttgagaa aaatgtcctg gactgctgca tttccctgct gactgagagc | 660 |
| tccctcaagc ccacagatag gagggacccc gtgctggtgt gcagggccat gtgtgctatg | 720 |
| atgagctttg agaaaggcca gggcgtgctc attgggaatt ggactgggga ctatgaaggt | 780 |
| ggcacagccc catacaagtg gacaggcagt gccccgatcc tgcagcagta ctacaacacg | 840 |
| aagcaggctg tgtgctttgg ccagtgctgg gtgtttgctg ggatcctgac tacagtgctg | 900 |
| agagcgttgg gcatcccagc acgcagtgtg acaggcttcg attcagctca cgacacagaa | 960 |
| aggaacctca cggtggacac ctatgtgaat gagaatggca agaaaatcac cagtatgacc | 1020 |
| cacgactctg tctggaattt ccatgtgtgg acggatgcct ggatgaagcg accggatctg | 1080 |
| cccaagggct acgacggctg gcaggctgtg gacgcaacgc cgcaggagcg aagccagggt | 1140 |
| gtcttctgct gtgggccatc accactgacc gccatccgca aaggtgacat ctttattgtc | 1200 |
| tatgacacca gattcgtctt ctcagaagtg aatggtgaca ggctcatctg gttggtgaag | 1260 |
| atggtgaatg ggcaggagga gttacacgta atttcaatgg agaccacaag catcgggaaa | 1320 |
| acatcagca ccaaggcagt gggccaagac aggcggagag atatcaccta tgagtacaag | 1380 |
| tatccagaag gctcctctga ggagaggcag gttcatggat catgccttcc tccttctcag | 1440 |
| ttctgagagg gagcacagac gacctgtaaa agagaacttt cttcacatgt cggtacaatc | 1500 |
| agatgatgtg ctgctgggaa actctgttaa tttcaccgtg attcttaaaa ggaagaccgc | 1560 |
| tgccctacag aatgtcaaca tcttgggctc ctttgaacta cagttgtaca ctggcaagaa | 1620 |
| gatggcaaaa ctgtgtgacc tcaataagac ctcgcagatc caaggtcaag tatcagaagt | 1680 |
| gactctgacc ttggactcca agacctacat caacagcctg gctatattag atgatgagcc | 1740 |
| agttatcaga ggtttcatca ttgcggaaat tgtggagtct aaggaaatca tggcctctga | 1800 |
| agtattcacg tcttttccagt accctgagtt ctctatagag ttgcctaaca caggcagaat | 1860 |

```
tggccagcta cttgtctgca attgtatctt caagaatacc ctggccatcc ccttgactga   1920
cgtcaagttc tctttggaaa gcctgggcat ctcctcacta cagacctctg accatgggtg   1980
agtctgcctg aggacggtgc agcctggtga gaccatccaa tcccaaataa aatgcaccc c   2040 aataaaaatg acccaagaa atttatcgtc aagttaagtt ccaaacaagt gaaagagatt    2100
aatgctcaga agattgttct catcaccaag tagccttgtc tgatgctgtg agccttagt    2160 tgagatttca gcatttccta ccttgtggct tagctttcag attatggatg attaaatttg   2220
atgacttata tgagggcaga ttcaagagcc agcaggtcaa aaaggccaac acaaccataa   2280
gcagccagac ccacaaggcc aggtcctgtg ctatcacagg gtcaccttct tttacagtta   2340
gaaacaccag ccgaggccac agaatcccat cccttt cctg agtcatggcc tcaaaaatca   2400
gggccaccat tgtctcaatt caaatccata gatttcgaag ccacagattc tctccctgga   2460
gcaagcatga ctatgggcag cccagtgctg ccacctgctg acgacccttg agaagctgcc   2520
atatcttcag gccatgggtt caccagccct gaaggcacct gtcaactgga gtgctctctc   2580
agcactggga tgggcctgat agaagtgcat tctcctccta ttgcctccat tctcctctct   2640
ctatccctga aatccaggaa gtccctctcc tggtgctcca agcagtttga agcccaatct   2700
gcaaggacat ttctcaaggg ccatgtggtt ttgcagacaa ccctgtcctc aggcctgaac   2760
tcaccataga gacccatgtc agcaaacggt gaccagcaaa tcctcttccc ttattctaaa   2820
gctgcccctt gggagactcc agggagaagg cattgcttcc tccctggtgt gaactctttc   2880
tttggtattc catccactat cctggcaact caaggctgct tctgttaact gaagcctgct   2940
ccttcttgtt ctgccctcca gagatttgct caaatgatca ataagcttta aattaaactc   3000
tacttcaaga aaaaaaaacc g                                             3021

<210> SEQ ID NO 7
<211> LENGTH: 267
<212> TYPE: DNA
<213> ORGANISM: Homo sapiens

<400> SEQUENCE: 7
gaacattcca gatacctatc attactcgat gctgttgata acagcaagat ggctttgaac    60
tcagggtcac caccagctat tggaccttac tatgaaaacc atggatacca accggaaaac   120
ccctatcccg cacagcccac tgtggtcccc actgtctacg aggtgcatcc ggctcagtac   180
tacccgtccc ccgtgcccca gtacgccccg agggtcctga cgcaggcttc caaccccgtc   240
gtctgcacgc agcccaaatc cccatcc                                       267

<210> SEQ ID NO 8
<211> LENGTH: 3443
<212> TYPE: DNA
<213> ORGANISM: Homo sapiens

<400> SEQUENCE: 8
gggcgggccg ggccgagtag gcgcgagcta agcaggaggc ggaggcggag gcggagggcg    60
aggggcgggg agcgccgcct ggagcgcggc aggtcatatt gaacattcca gatacctatc   120
attactcgat gctgttgata acagcaagat ggctttgaac tcagggtcac caccagctat   180
tggaccttac tatgaaaacc atggatacca accggaaaac ccctatcccg cacagcccac   240
tgtggtcccc actgtctacg aggtgcatcc ggctcagtac tacccgtccc ccgtgcccca   300
gtacgccccg agggtcctga cgcaggcttc caaccccgtc gtctgcacgc agcccaaatc   360
```

-continued

| | |
|---|---|
| cccatccggg acagtgtgca cctcaaagac taagaaagca ctgtgcatca ccttgaccct | 420 |
| ggggaccttc ctcgtgggag ctgcgctggc cgctggccta ctctggaagt tcatgggcag | 480 |
| caagtgctcc aactctggga tagagtgcga ctcctcaggt acctgcatca acccctctaa | 540 |
| ctggtgtgat ggcgtgtcac actgccccgg cggggaggac gagaatcggt gtgttcgcct | 600 |
| ctacggacca aacttcatcc ttcaggtgta ctcatctcag aggaagtcct ggcaccctgt | 660 |
| gtgccaagac gactggaacg agaactacgg gcgggcggcc tgcagggaca tgggctataa | 720 |
| gaataatttt tactctagcc aaggaatagt ggatgacagc ggatccacca gctttatgaa | 780 |
| actgaacaca agtgccggca atgtcgatat ctataaaaaa ctgtaccaca gtgatgcctg | 840 |
| ttcttcaaaa gcagtggttt ctttacgctg tatagcctgc ggggtcaact tgaactcaag | 900 |
| ccgccagagc aggatcgtgg gcggcgagag cgcgctcccg ggggcctggc cctgggcagg | 960 |
| tcagcctgca cgtccagaac gtccacgtgt gcggaggctc catcatcacc cccgagtgga | 1020 |
| tcgtgacagc cgcccactgc gtggaaaaac ctcttaacaa tccatggcat tggacggcat | 1080 |
| ttgcggggat tttgagacaa tctttcatgt tctatggagc cggataccaa gtagaaaaag | 1140 |
| tgatttctca tccaaattat gactccaaga ccaagaacaa tgacattgcg ctgatgaagc | 1200 |
| tgcagaagcc tctgactttc aacgacctag tgaaaccagt gtgtctgccc aacccaggca | 1260 |
| tgatgctgca gccagaacag ctctgctgga tttccgggtg ggggccacc gaggagaaag | 1320 |
| ggaagacctc agaagtgctg aacgctgcca aggtgcttct cattgagaca cagagatgca | 1380 |
| acagcagata tgtctatgac aacctgatca caccagccat gatctgtgcc ggcttcctgc | 1440 |
| aggggaacgt cgattcttgc caggtgaca gtggagggcc tctggtcact tcgaagaaca | 1500 |
| atatctggtg gctgataggg gatacaagct ggggttctgg ctgtgccaaa gcttacagac | 1560 |
| caggagtgta cgggaatgtg atggtattca cggactggat ttatcgacaa atgaggggcag | 1620 |
| acggctaatc cacatggtct tcgtccttga cgtcgtttta caagaaaaca atggggctgg | 1680 |
| ttttgcttcc ccgtgcatga tttactctta gagatgattc agaggtcact tcatttttat | 1740 |
| taaacagtga acttgtctgg cttttggcact ctctgccatt ctgtgcaggc tgcagtggct | 1800 |
| ccccctgccca gcctgctctc cctaaccct tgtccgcaag gggtgatggc cggctggttg | 1860 |
| tgggcactgg cggtcaagtg tggaggagag gggtggaggc tgccccattg agatcttcct | 1920 |
| gctgagtcct ttccaggggc caattttgga tgagcatgga gctgtcacct ctcagctgct | 1980 |
| ggatgacttg agatgaaaaa ggagagacat ggaaagggag acagccaggt ggcacctgca | 2040 |
| gcggctgcct ctggggccac ttggtagtgt ccccagccta cctctccaca aggggatttt | 2100 |
| gctgatgggt tcttagagcc ttagcagccc tggatggtgg ccagaaataa agggaccagc | 2160 |
| ccttcatggg tggtgacgtg gtagtcacct tgtaagggga acagaaacat ttttgttctt | 2220 |
| atggggtgag aatatagaca gtgcccttgg gtgcgaggga agcaattgaa aaggaacttg | 2280 |
| ccctgagcac tcctggtgca ggtctccacc tgcacattgg gtgggctcc tgggagggag | 2340 |
| actcagcctt cctcctcatc ctccctgacc ctgctcctag caccctggag agtgcacatg | 2400 |
| ccccttggtc ctgggcaggg gcgccaagtc tggcaccatg ttggcctctt caggcctgct | 2460 |
| agtcactgga aattgaggtc catggggaa atcaaggatg ctcagtttaa ggtacactgt | 2520 |
| ttccatgtta tgtttctaca cattgctacc tcagtgctcc tggaaactta gcttttgatg | 2580 |
| tctccaagta gtccaccttc atttaactct ttgaaactgt atcatctttg ccaagtaaga | 2640 |
| gtggtggcct atttcagctg ctttgacaaa atgactggct cctgacttaa cgttctataa | 2700 |
| atgaatgtgc tgaagcaaag tgcccatggt ggcggcgaag aagagaaaga tgtgttttgt | 2760 |

-continued

```
tttggactct ctgtggtccc ttccaatgct gtgggtttcc aaccagggga agggtccctt    2820
ttgcattgcc aagtgccata accatgagca ctactctacc atggttctgc ctcctggcca    2880
agcaggctgg tttgcaagaa tgaaatgaat gattctacag ctaggactta accttgaaat    2940
ggaaagtctt gcaatcccat ttgcaggatc cgtctgtgca catgcctctg tagagagcag    3000
cattcccagg gaccttggaa acagttggca ctgtaaggtg cttgctcccc aagacacatc    3060
ctaaaaggtg ttgtaatggt gaaaacgtct tccttcttta ttgccccttc ttatttatgt    3120
gaacaactgt ttgtcttttt ttgtatcttt tttaaactgt aaagttcaat tgtgaaaatg    3180
aatatcatgc aaataaatta tgcgattttt ttttcaaagt aaccactgca tctttgaagt    3240
tctgcctggt gagtaggacc agcctccatt tccttataag ggggtgatgt tgaggctgct    3300
ggtcagagga ccaaaggtga ggcaaggcca gacttggtgc tcctgtggtt ggtgccctca    3360
gttcctgcag cctgtcctgt tggagaggtc cctcaaatga ctccttctta ttattctatt    3420
agtctgtttc catgggcgtg ata                                            3443
```

<210> SEQ ID NO 9
<211> LENGTH: 254
<212> TYPE: DNA
<213> ORGANISM: Homo sapiens

<400> SEQUENCE: 9

```
gtgctgcacc aggccaccat cctgcccaag actgggacag tgtccctgga ggtacggctc     60
ctggaggcct cccgtgcctt cgaggtgtca gagaacggca acctggtagt gagtgggaag    120
gtgtaccagt gggatgaccc tgaccccagg ctcttcgacc accggaaag ccccaccccc    180 aaccccacgg agccctctt cctggcccag gctgaagttt acaaggagct gcgtctgcgt    240
ggctacgact acgg                                                      254
```

<210> SEQ ID NO 10
<211> LENGTH: 8470
<212> TYPE: DNA
<213> ORGANISM: Homo sapiens
<220> FEATURE:
<221> NAME/KEY: misc_feature
<222> LOCATION: (4131)..(4131)
<223> OTHER INFORMATION: n=a, c, g or t
<220> FEATURE:
<221> NAME/KEY: misc_feature
<222> LOCATION: (5117)..(5117)
<223> OTHER INFORMATION: n=a, c, g or t
<220> FEATURE:
<221> NAME/KEY: misc_feature
<222> LOCATION: (5552)..(5552)
<223> OTHER INFORMATION: n=a, c, g or t

<400> SEQUENCE: 10

```
cggccgtcga cacggcagcg gccccggcct ccctctccgc cgcgcttcag cctcccgctc     60
cgccgcgctc cagcctcgct ctccgccgcc cgcaccgccg cccgcgccct caccagagca    120
gccatggagg aggtggtgat tgccggcatg tccgggaagc tgccagagtc ggagaacttg    180
caggagttct gggacaacct catcggcggt gtggacatgg tcacggacga tgaccgtcgc    240
tggaaggcgg ggctctacgg cctgcccgg cggtccggca agctgaagga cctgtctagg    300
tttgatgcct ccttcttcgg agtccacccc aagcaggcac acacgatgga ccctcagctg    360
cggctgctgc tggaagtcac ctatgaagca atcgtggacg gaggcatcaa cccagattca    420
ctccgaggaa cacacactgg cgtctgggtg ggcgtgagcg gctctgagac ctcggaggcc    480
```

```
ctgagccgag accccgagac actcgtgggc tacagcatgg tgggctgcca gcgagcgatg    540
atggccaacc ggctctcctt cttcttcgac ttcagagggc ccagcatcgc actggacaca    600
gcctgctcct ccagcctgat ggccctgcag aacgcctacc aggccatcca cagcgggcag    660
tgccctgccg ccatcgtggg gggcatcaat gtcctgctga agcccaacac ctccgtgcag    720
ttcttgaggc tggggatgct cagccccgag ggcacctgca aggccttcga cacagcgggg    780
aatgggtact gccgctcgga gggtgtggtg gccgtcctgc tgaccaagaa gtccctggcc    840
cggcgggtgt acgccaccat cctgaacgcc ggcaccaata cagatggctt caaggagcaa    900
ggcgtgacct tcccctcagg ggatatccag gagcagctca tccgctcgtt gtaccagtcg    960
gccggagtgg cccctgagtc atttgaatac atcgaagccc acggcacagg caccaaggtg   1020
ggcgaccccc aggagctgaa tggcatcacc cgagccctgt cgccacccg ccaggagccg   1080
ctgctcatcg gctccaccaa gtccaacatg gggcacccgg agccagcctc ggggctggca   1140
gccctggcca aggtgctgct gtccctggag cacgggctct gggcccccaa cctgcacttc   1200
catagcccca accctgagat cccagcgctg ttggatgggc ggctgcaggt ggtggaccag   1260
cccctgcccg tccgtggcgg caacgtgggc atcaactcct ttggcttcgg gggctccaaa   1320
cgtgcacatc atcctgaggc ccaacacgca gccgcccccc gcacccggcc cacatgccac   1380
cctgccccgt ctgctgcggg ccagcggacg caccccgag gccgtgcaga agctgctgga   1440
gcagggcctc cggcacagcc agggcctggc tttcctgagc atgtgaacga catcgcggct   1500
gtccccgacc accgccatgc ccttccgtgg ctacgctgtg ctgggtggtg agacgcggtg   1560
gcccagaggt gcagcaggtg cccgctggcg agcgcccgct ctggttcatc tgctctggga   1620
tgggcacaca gtgcgcgggg atggggctga gcctcatgcg cctggaccgc ttccgagatt   1680
ccatcctacg ctccgatgag gctgtgaacc gattcggcct gaaggtgtca cagctgctgc   1740
tgagcacaga cgagagcacc tttgatgaca tcgtccattc gtttgtgagc ctgactgcca   1800
tccagatagg cctcatagac ctgctgagct gcatgggggct gaggccagat ggcatcgtcg   1860
gccactccct gggggaggtg gcctgtggct acgccgacgg ctgcctgtcc caggaggagg   1920
ccgtcctcgc tgcctactgg aggggacagt gcatcaaaga agcccatctc ccgccgggcg   1980
ccatggcagc cgtgggcttg tcctgggagg agtgtaaaca gcgctgcccc ccggcggtgg   2040
tgcccgccgc cacaactcca aggacacagt caccatctcg ggacctcagg ccccggtgtt   2100
tgagttcgtg gagcagctga ggaaggaggg tgtgttttgcc aaggaggtgc ggaccggcgg   2160
tatgccttc cactcctact tcatggaggc catcgcaccc ccactgctgc aggagctcaa   2220
gaaggtgatc cggagccga agccacgttc agcccgctgg ctcagcacct ctatccccga   2280
ggcccagtgg cacagcagcc tggcacgcac gtcctccgcc gagtacaatg tcaacaacct   2340
ggtgagccct gtgctgttcc aggaggccct gtggcacgtg cctgagcacg cggtggtgct   2400
ggagatcgcg cccacgccc tgctgcaggc tgtcctgaag cgtggcctga gccgagctg   2460
caccatcatc cccctgatga agaaggatca cagggacaac ctggagttct tcctggccgg   2520
catcggcagg ctgcacctct caggcatcga cgccaacccc aatgccttgt cccacctgt   2580
ggagtcccca gctccccgag gaactccccct catctcccca ctcatcaagt gggaccacag   2640
cctggcctgg gacgcgccgg ccgccgagga cttccccaac ggttcaggtt cccctcagc   2700
caccatctac acatgcacac caagctccga gtctcctgac cgctacctgg tggaccacac   2760
catcgacggt cgcgtcctct tccccgccac tggctacctg agcatagtgt ggaagacgct   2820
ggccccgaccc ctgggcctgg gcgtcgagca gctgcctgtg gtgtttgagg atgtggtgct   2880
```

-continued

```
gcaccaggcc accatcctgc caagactgg gacagtgtcc ctggaggtac ggctcctgga      2940
ggcctcccgt gccttcgagg tgtcagagaa cggcaacctg gtagtgagtg ggaaggtgta      3000
ccagtgggat gaccctgacc ccaggctctt cgaccacccg gaaagcccca ccccaaccc      3060 cacggagccc ctcttcctgg cccaggctga agtttacaag gagctgcgtc tgcgtggcta      3120
cgactacgcc cctcatttcc agggcatcct ggaggccagc ctggaaggtg actcggggag      3180
gctgctgtgg aaggataatg ggtgagttca tggacaccat gctgcagatg tccatcctgg      3240
gtcggccaag cacggcctgt acctgcccac ccgtgtcacc gccatccaca tcgaccctgc      3300
cacccacagg cagaagctgt acacactgca ggacaaggcc caagtggctg acgtggtggt      3360
gagcaggtgg ctgagggtca cagtggccgg aggcgtccac atctccgggc tccacactga      3420
gtcggccccg cggcggcagc aggagcagca ggtgcccatc ctggagaagt tttgcttcac      3480
tccccacacg gaggagggggt gcctgtctga gcacgctgcc ctcgaggagg agctgcaact      3540
gtgcaagggg ctggtcgagg cactcgagac caaggtgacc cagcaggggc tgaagatggt      3600
ggtgcccgga ctggatgggg cccagatccc cccgggaccc ctcacagcag gaactgcccc      3660
ggctgttgtc ggctgcctgc aggcttcagc tcaacgggaa cctgcagctg gagctggcgc      3720
aggtgctggc ccaggagagg cccaagctgc cagaggaccc tctgctcagc ggcctcctgg      3780
actccccggc actcaaggcc tgcctggaca ctgccgtgga aacatgcccc agcctgaaga      3840
tgaaggtggt ggaggtgctg gccggccacg gtcacctgta ttcccgcatc ccaggcctgc      3900 tcagcccca tccctgctg cagctgagct acacggccac cgaccgccac ccccaggccc      3960
tggaggctgc ccaggccgag ctgcagcagc acgacgttgc ccagggccag tgggatcccg      4020
cagaccctgc ccccagcgcc ctgggcagcg cggacctcct ggtgtgcaac tgtgctgtgg      4080
ctgccctcgg ggaccccgcct cagctctcag caacatggtg gctgccctga nagaagggg      4140 cttctgctc ctgcacacac tgctccgggg gcacccctc gggacatcg tggccttcct      4200 cacctccact gagccgcagt atggccaggg catcctgagc caggacgcgt gggagagcct      4260
cttctccagg gtgtcgctgc gcctggtggg cctgaagaag tccttctacg gctccacgct      4320
cttcctgtgc cgccggccca ccccgcagga cagcccccatc ttcctgccgg tggacgatac      4380
cagcttccgt tgggtggagt ctctgaaggg catcctggct gacgaagact cttccccggc      4440
ctgtgtggct gaaggccatc aactgttcca cctcgggcgt ggtgggcttg gtgaactgtc      4500
tccgccgaga gccggcgga acgctccggt gtgtgctgct ctccaacctc agcagcacct      4560
cccacgtccc ggaggtggac ccgggctccg cagaactgca gaaggtgttg cagggagacc      4620
tggtgatgaa cgtctaccgc gacggggcct ggggggcttt ccgccacttc ctgctggagg      4680
aggacaagcc tgaggagccg acggcacatg cctttgtgag caccctcacc cggggggacc      4740
tgtccctcca tccgctgggt ctgctcctcg ctgcgccatg cccagcccac ctgccctggc      4800
gcccagctct gcacggtcta ctacgcctcc ctcaacttcc gcgacatcat gctggccact      4860
ggcaagctgt cccctgatgc catcccaggg aagtggacct cccaggacag cctgctaggt      4920
atggagttct cgggccgaga cgccagcggc aagcgtgtga tgggactggt gcctgccaag      4980
ggcctggcca cctctgtcct gctgtcaccg gacttcctct gggatgtgcc ttccaactgg      5040
acgctggagg aggcggcctc ggtgcctgtc gtctacagca cggcctacta cgcgctggtg      5100
gtgcgtgggc gggtgcncc cggggagacg ctgctcatcc actcgggctc gggcggcgtg      5160
ggccaggccg ccatcgccat cgccctcagt ctgggctgcc gcgtcttcac caccgtgggg      5220
```

```
tcggctgaga agcgggcgta cctccaggcc aggttccccc agctcgacag caccagcttc    5280
gccaactccc gggacacatc cttcgagcag catgtgctgt ggcacacggg cgggaagggc    5340
gttgacctgg tcttgaactc cttggcggaa gagaagctgc aggccagcgt gaggtgcttg    5400
gctacgcacg gtcgcttcct ggaaattggc aaattcgacc tttctcagaa ccacccgctc    5460
ggcatggcta tcttcctgaa gaacgtgaca ttccacgggg tcctactgga tgcgttcttc    5520
aacgagagca gtgctgactg gcgggaggtg tnggcgcttg tgcaggccgg catccgggat    5580
ggggtggtac ggcccctcaa gtgcacggtg ttccatgggg cccaggtgga ggacgccttc    5640
cgctacatgg cccaagggaa gcacattggc aaagtcgtcg tgcaggtgct tgcggaggag    5700
ccggaggcag tggctgaagg gggccaaacc caagctgatg tcggccatct ccaagacctt    5760
ctgcccggcc cacaagagct acatcatcgc tggtggtctg ggtggcttcg gcctggagtt    5820
ggcgcagtgg ctgatacagc gtggggtgca gaagctcgtg ttgacttctc gctccgggat    5880
ccggacaggc taccaggcca agcaggtccg ccggtggagg cgccagggcg tacaggtgca    5940
ggtgtccacc agcaacatca gctcactgga gggggcccgg ggcctcattg ccgaggcggc    6000
gcagcttgag gcccgtgggc ggcgtcttca acctggccgt ggtcttgaga gatggcttgc    6060
tggagaacca gaccccagag ttcttccagg acgtctgcaa gcccaagtac agcggcaccc    6120
tgaacctgga cagggtgacc cgagggcgtg ccctgagctg gactactttg tggtcttctc    6180
ctctgtgagc tgcgggcgtg gcaatgcggg acagagcaac tacggctttg ccaatttccg    6240
ccatggagcg tatctgtgag aaacgccggc acgaaggcct cccaggcctg gccgtgcagt    6300
ggggcgccat cggcgacgtg ggcattttgg tggagacgat gagcaccaac gacacgatcg    6360
tcagtggcac gctgccccag cgcatggcgt cctgcctgga ggtgctggac ctcttcctga    6420
accagcccca catggtcctg agcagctttg tgctggctga gaaggctgcg gcctataggg    6480
acagggacag ccagcgggac ctggtggagg ccgtggcaca catcctgggc atccgcgact    6540
tggctgctgt caacctggac agctcactgg cggacctggg cctggactcg ctcatgagcg    6600
tggaggtgcg ccagacgctg gagcgtgagc tcaacctggt gctgtccgtg cgcgaggtgc    6660
ggcaactcac gctccggaaa ctgcaggagc tgtcctcaaa ggcggatgag gccagcgagc    6720
tgggcatgcc ccacgcccaa ggaggatggt ctggcccagc agcagactca gctgaacctg    6780
cgctccctgc tggtgaaccc ggagggcccc accctgatgc ggctcaactg ccgtgcagag    6840
ctcggagcgg cccctgttcc tggtgcaccc aattcgaggg ctccaccacc gtgttccaca    6900
gcctggcctc ccggctcagc atccccacct atggcctgca gtgcacccga gctgcgcccc    6960
ttgacagcat ccacagcctg gctgcctact acatcgactg catcaggcag gtgcagcccg    7020
agggcccctt ccgcgtggcc ggctactcct acggggcctg cgtggccttt gaaatgtgct    7080
cccagctgca ggcccagcag agcccagccc ccacccacaa cagcctcttc ctgttcgacg    7140
gctcgcccac ctacgtactg gcctacaccc agagctaccg gcaaagctg acccaggct    7200 gtgaggctga ggctgagacg gaggccatat gcttcttcgt gcagcagttc acggacatgg    7260
agcacaacag ggtgctggag gcgctgctgc cgctgaaggg cctagaggag cgtgtggcag    7320
ccgccgtgga cctgatcatc aagagccacc agggcctgga ccgccaggag ctgagctttg    7380
cggcccggtc cttctactac aagctgcgtg ccgctgagca gtacaaccc aaggccaagt    7440 accatggcaa cgtgatgcta ctgcgcgcca agacgggtgg cgcctacggc gaggacctgg    7500
gcgcggacta caacctctcc caggtatgcg acggaaagt atccgtccac gtcatcgagg    7560
gtgaccaccg cacgctgctg gagggcagcg gcctggagtc catcatcagc atcatccaca    7620
```

-continued

```
gctccctggc tgagccacgc gtgagcgtgc gggagggcta ggcccgtgcc cccgcctgcc    7680
accggaggtc actccaccat ccccaccccca tcccacccca ccccgccat gcaacgggat    7740 tgaagggtcc tgccggtggg accctgtccg gcccagtgcc actgccccc gaggctagct    7800 agacgtaggt gttaggcatg tcccacccac ccgccgcctc ccacggcacc tcggggacac    7860
cagagctgcc gacttggaga ctcctggtct gtgaagagcc ggtggtgccc gtgcccgcag    7920 gaactgggc tgggcctcgt gcgcccgtgg ggtctgcgct tggtctttct gtgcttggat    7980
ttgcatattt attgcattgc tggtagagac ccccaggcct gtccaccctg ccaagactcc    8040
tcaggcagcg tgtgggtccc gcactctgcc cccatttccc cgatgtcccc tgcgggcgcg    8100
ggcagccacc caagcctgct ggctgcggcc ccctctcggc caggcattgg ctcagcccgc    8160
tgagtggggg gtcgtgggcc agtccccgag gactgggccc ctgcacaggc acacagggcc    8220
cggccacacc cagcggcccc ccgcacagcc accgtggggg tgctgccctt atgcccggcg    8280
ccgggcacca actccatgtt tggtgttgt ctgtgtttgt ttttcaagaa atgattcaaa    8340
ttgctgcttg gattttgaaa tttactgtaa ctgtcagtgt acacgtctgg accccgtttc    8400 attttttacac caatttggta aaaatgctgc tctcagcctc ccacaattaa accgcatgtg    8460
atctccaaaa                                                           8470
```

<210> SEQ ID NO 11
<211> LENGTH: 812
<212> TYPE: DNA
<213> ORGANISM: Homo sapiens

<400> SEQUENCE: 11

```
gccgcagcca atcagcgcgc gtgcccgggc ccctgcgtct cttgcgtcaa gacggccgtg     60
ctgagcgaat gcaggcgact tgcgagctgg gagcgattta aaacgctttg gattcccccg    120
gcctgggtgg ggagagcgag ctgggtgccc cctagattcc ccgcccccgc acctcatgag    180
ccgaccctcg gctccatgga gcccggcaat tatgccacct tggatggagc caaggatatc    240
gaaggcttgc tgggagcggg aggggggcgg aatctggtcg cccactcccc tctgaccagc    300
cacccagcgg cgcctacgct gatgcctgct gtcaactatg ccccttgga tctgccaggc    360 tcggcggagc gccaaagcaa tgccacccat gccctgggt gccccagggg acgtccccag    420
ctcccgtgcc ttatggttac tttggaggcg ggtactactc ctgccgagtg tcccggagct    480
cgctgaaacc ctgtgcccag gcagccaccc tggccgcgta cccgcggag actcccacgg    540 ccggggaaga gtaccccagc cgcccactg agtttgcctt ctatccggga tatccgggaa    600
cctaccagcc tatggccagt tacctggacg tgtctgtggt gcagactctg ggtgctcctg    660
gagaaccgcg acatgactcc ctgttgcctg tggacagtta ccagtcttgg gctctcgctg    720
gtggctggaa cagccagatg tgttgccagg gagaacagaa cccaccaggt ccctttggga    780
aggcagcatt tgcagactcc agcgggcagc ac                                  812
```

<210> SEQ ID NO 12
<211> LENGTH: 2385
<212> TYPE: DNA
<213> ORGANISM: Homo sapiens

<400> SEQUENCE: 12

```
ataagctggg gtaaagtatt ttcgcagttt ctgcctttag gatttatta gcttctctcc     60 cccaggccgc agccaatcag cgcgcgtgcc cggggccctg cgtctcttgc gtcaagacgg    120
```

| | |
|---|---|
| ccgtgctgag cgaatgcagg cgacttgcga gctgggagcg atttaaaacg ctttggattc | 180 |
| ccccggcctg ggtggggaga gcgagctggg tgccccctag attccccgcc cccgcacctc | 240 |
| atgagccgac cctcggctcc atggagcccg gcaattatgc caccttggat ggagccaagg | 300 |
| atatcgaagg cttgctggga gcgggagggg ggcggaatct ggtcgccacc tcccctctga | 360 |
| ccagccaccc agcggcgcct acgctgatgc ctgctgtcaa ctatgccccc ttggatctgc | 420 |
| caggctcggc ggagccgcca agcaatgcc acccatgccc tggggtgccc caggggacgt | 480 |
| ccccagctcc cgtgccttat ggttactttg gaggcgggta ctactcctgc cgagtgtccc | 540 |
| ggagctcgct gaaaccctgt gcccaggcag ccaccctggc cgcgtacccc gcggagactc | 600 |
| ccacggccgg ggaagagtac cccagccgcc ccactgagtt tgccttctat ccgggatatc | 660 |
| cgggaaccta ccagcctatg gccagttacc tggacgtgtc tgtggtgcag actctgggtg | 720 |
| ctcctggaga accgcgacat gactccctgt tgcctgtgga cagttaccag tcttgggctc | 780 |
| tcgctggtgg ctggaacagc cagatgtgtt gccaggagga acagaaccca ccaggtccct | 840 |
| tttggaaggc agcatttgca gactccagcg ggcagcaccc tcctgacgcc tgcgcctttc | 900 |
| gtcgcggccg caagaaacgc attccgtaca gcaaggggca gttgcgggag ctggagcggg | 960 |
| agtatgcggc taacaagttc atcaccaagg acaagaggcg caagatctcg gcagccacca | 1020 |
| gcctctcgga gcgccagatt accatctggt ttcagaaccg ccgggtcaaa gagaagaagg | 1080 |
| ttctcgccaa ggtgaagaac agcgctaccc cttaagagat ctccttgcct gggtgggagg | 1140 |
| agcgaaagtg ggggtgtcct ggggagacca ggaacctgcc aagcccaggc tggggccaag | 1200 |
| gactctgctg agaggcccct agagacaaca cccttcccag gccactggct gctggactgt | 1260 |
| tcctcaggag cggcctgggt acccagtatg tgcaggagga cggaacccca tgtgacagcc | 1320 |
| cactccacca gggttcccaa agaacctggc ccagtcataa tcattcatcc tgacagtggc | 1380 |
| aataatcacg ataaccagta ctagctgcca tgatcgttag cctcatattt tctatctaga | 1440 |
| gctctgtaga gcactttaga aaccgctttc atgaattgag ctaattatga ataaatttgg | 1500 |
| aaggcgatcc ctttgcaggg aagctttctc tcagaccccc ttccattaca cctctcaccc | 1560 |
| tggtaacagc aggaagactg aggagagggg aacgggcaga ttcgttgtgt ggctgtgatg | 1620 |
| tccgtttagc attttctca gctgacagct gggtaggtgg acaattgtag aggctgtctc | 1680 |
| ttcctccctc cttgtccacc ccataggtg tacccactgg tcttggaagc acccatcctt | 1740 |
| aatacgatga tttttctgtc gtgtgaaaat gaagccagca ggctgcccct agtcagtcct | 1800 |
| tccttccaga gaaaaagaga tttgagaaag tgcctgggta attcaccatt aatttcctcc | 1860 |
| cccaaactct ctgagtcttc ccttaatatt tctggtggtt ctgaccaaag caggtcatgg | 1920 |
| tttgttgagc atttgggatc ccagtgaagt agatgtttgt agccttgcat acttagccct | 1980 |
| tcccaggcac aaacggagtg gcagagtggt gccaaccctg ttttcccagt ccacgtagac | 2040 |
| agattcacgt gcggaattct ggaagctgga gacagacggg ctctttgcag agccgggact | 2100 |
| ctgagaggga catgagggcc tctgcctctg tgttcattct ctgatgtcct gtacctgggc | 2160 |
| tcagtgcccg gtgggactca tctcctggcc gcgcagcaaa gccagcgggt tcgtgctggt | 2220 |
| ccttcctgca ccttaggctg ggggtggggg gcctgccggc gcattctcca cgattgagcg | 2280 |
| cacaggcctg aagtctggac aacccgcaga accgaagctc cgagcagcgg gtcggtggcg | 2340 |
| agtagtgggg tcggtggcga gcagttggtg gtgggccgcg gccgc | 2385 |

<210> SEQ ID NO 13
<211> LENGTH: 221

<212> TYPE: DNA
<213> ORGANISM: Homo sapiens
<220> FEATURE:
<221> NAME/KEY: misc_feature
<222> LOCATION: (4)..(4)
<223> OTHER INFORMATION: n=a, c, g or t

<400> SEQUENCE: 13

| | | | | | |
|---|---|---|---|---|---|
| dsdnrstatc | tttctgtgtg | gtgcagccct | gttggcagtg | ggcatctggg | tgtcaatcga | 60 |
| tggggcatcc | tttctgaaga | tcttcgggcc | actgtcgtcc | agtgccatgc | agtttgtcaa | 120 |
| cgtgggctac | ttcctcatcg | cagccggcgt | tgtggtcttt | gctcttggtt | tcctgggctg | 180 |
| ctatggtgct | aagactgaga | gcaagtgtgc | cctcgtgacg | t | | 221 |

<210> SEQ ID NO 14
<211> LENGTH: 1533
<212> TYPE: DNA
<213> ORGANISM: Homo sapiens

<400> SEQUENCE: 14

| | | | | | |
|---|---|---|---|---|---|
| gggcacgcag | acattctggg | aagccacttg | ccccacccct | gggctgcttc | ttcttgagat | 60 |
| caggagggc | gttgcccagg | gctggtgttg | ccaggtggag | gcctgctgag | gcagtggttg | 120 |
| tgggatcgg | tctccaggca | gcaggggca | gcagggtcaa | ggagaggcta | actggccacg | 180 |
| ggtgggcca | gcaggcgggc | agaaggaggc | tttaaagcgc | ctaccctgcc | tgcaggtgag | 240 |
| cagtggtgtg | tgagagccag | gccgtccctc | tgcctgccca | ctcagtggca | acacccggga | 300 |
| gctgttttgt | cctttgtgga | gcctcagcag | ttccctgctt | tcagaactca | ctgccaagag | 360 |
| ccctgaacag | gagccaccat | ggcagtgctt | cagcttcatt | aagaccatga | tgatcctctt | 420 |
| caatttgctc | atctttctgt | gtggtgcagc | cctgttggca | gtgggcatct | gggtgtcaat | 480 |
| cgatggggca | tcctttctga | agatcttcgg | gccactgtcg | tccagtgcca | tgcagtttgt | 540 |
| caacgtgggc | tacttcctca | tcgcagccgg | cgttgtggtc | tttgctcttg | gtttcctggg | 600 |
| ctgctatggt | gctaagactg | agagcaagtg | tgccctcgtg | acgttcttct | tcatcctcct | 660 |
| cctcatcttc | attgctgagg | ttgcagctgc | tgtggtcgcc | ttggtgtaca | ccacaatggc | 720 |
| tgagcacttc | ctgacgttgc | tggtagtgcc | tgccatcaag | aaagattatg | gttcccagga | 780 |
| agacttcact | caagtgtgga | acaccaccat | gaaagggctc | aagtgctgtg | gcttcaccaa | 840 |
| ctatacggat | tttgaggact | caccctactt | caaagagaac | agtgcctttc | ccccattctg | 900 |
| ttgcaatgac | aacgtcacca | acacagccaa | tgaaacctgc | accaagcaaa | aggctcacga | 960 |
| ccaaaaagta | gagggttgct | tcaatcagct | tttgtatgac | atccgaacta | atgcagtcac | 1020 |
| cgtgggtggt | gtggcagctg | gaattggggg | cctcgagctg | gctgccatga | ttgtgtccat | 1080 |
| gtatctgtac | tgcaatctac | aataagtcca | cttctgcctc | tgccactact | gctgccacat | 1140 |
| gggaactgtg | aagaggcacc | ctggcaagca | gcagtgattg | ggggagggga | caggatctaa | 1200 |
| caatgtcact | tgggccagaa | tggacctgcc | ctttctgctc | cagacttggg | gctagatagg | 1260 |
| gaccactcct | tttaggcgat | gcctgacttt | ccttccattg | gtgggtggat | gggtgggggg | 1320 |
| cattccagag | cctctaaggt | agccagttct | gttgcccatt | ccccagtct | attaaaccct | 1380 |
| tgatatgccc | cctaggccta | gtggtgatcc | cagtgctcta | ctggggatg | agagaaaggc | 1440 |
| attttatagc | ctgggcataa | gtgaaatcag | cagagcctct | gggtggatgt | gtagaaggca | 1500 |
| cttcaaaatg | cataaacctg | ttacaatgtt | gcc | | | 1533 |

<210> SEQ ID NO 15

<211> LENGTH: 472
<212> TYPE: DNA
<213> ORGANISM: Homo sapiens

<400> SEQUENCE: 15

```
tcagagaaaa ctcaaacttt attgagagaa ttttcaaatt ttcagtcaca ttttcaatgt      60
gacatcagcc atgtgtgtag cttcagcttg tcttcttttt aacttatggc tgcccatctc     120
ctgcttcttt agtcttagca tgcttaggat taggtggagt cttctctttt acatcagagc     180
catctccacg ctcactccga gtctttccca gatccatttc ctggcaatca ccttctactt     240
tacgttcttc gatcggaggt gttccttctc tctcttgtcc aggttcaata tcctgattgt     300
cagttggtgg ttcctcttgc tgagattcac cgggagccac gaatgcaacc acatcgggag     360
cctcctgacc atctcctctt cctctggatc ttgatctcac tcgtgcactc atcgctgcaa     420
ctagaagatc gtgaactgaa gaacttgagt cagcagagag cctggcgaag aa             472
```

<210> SEQ ID NO 16
<211> LENGTH: 478
<212> TYPE: DNA
<213> ORGANISM: Homo sapiens

<400> SEQUENCE: 16

```
cttcattctt cgccaggctc tctgctgact caagttcttc agttcacgat cttctagttg      60
cagcgatgag tgcacgagtg agatcaagat ccagaggaag aggagatggt caggaggctc     120
ccgatgtggt tgcattcgtg gctcccggtg aatctcagca agaggaacca ccaactgaca     180
atcaggatat tgaacctgga caagagagag aaggaacacc tccgatcgaa gaacgtaaag     240
tagaaggtga ttgccaggaa atggatctgg aaaagactcg gagtgagcgt ggagatggct     300
ctgatgtaaa agagaagact ccacctaatc ctaagcatgc taagactaaa gaagcaggag     360
atgggcagcc ataagttaaa aagaagacaa gctgaagcta cacacatggc tgatgtcaca     420
ttgaaaatgt gactgaaaat ttgaaaattc tctcaataaa gtttgagttt tctctgaa       478
```

<210> SEQ ID NO 17
<211> LENGTH: 198
<212> TYPE: DNA
<213> ORGANISM: Homo sapiens
<220> FEATURE:
<221> NAME/KEY: misc_feature
<222> LOCATION: (191)..(191)
<223> OTHER INFORMATION: n=a, c, g or t

<400> SEQUENCE: 17

```
cccgctgtac caccccagca tgttctgcgc cggcggaggg caagaccaga aggactcctg      60
caacggtgac tctgggggggc ccctgatctg caacgggtac ttgcagggcc ttgtgtcttt     120
cggaaaagcc ccgtgtggcc aagttggcgt gccaggtgtc tacaccaacc tctgcaaatt     180
cactgagtgg nattaagg                                                   198
```

<210> SEQ ID NO 18
<211> LENGTH: 465
<212> TYPE: DNA
<213> ORGANISM: Homo sapiens

<400> SEQUENCE: 18

```
tggagatgga gtatgtattt atttacaaa aataaatcac catcttcgga ccatttgtag       60
actggaacat ttcgagcaat gagtgcgcca cacggacgtg tgccctggtg actccctgat     120
gttcgcgtca cccccagggc caccttggcg cccgcatgag cctcgcttcc cactcccggc     180
```

```
ctccaactcc cttccctcgc agccgccatt caccttctgc tgtttatttg tctgcagagc    240
gcctggacac cggaaaaggc gattccctga gcgcctggag ttggagacaa ttcctggttc    300
agaatttaaa catctttcta aggtaagcgc tgctccaaaa ctcttcgccg cgtggggact    360
ttgcaccagg ggcggttggg aaggaagttg gccctccacg ggttcctggg caaccgcggc    420
ctgttgaaaa aaggttctgg gtcaaataat ttaacttcgg aggag                    465
```

<210> SEQ ID NO 19
<211> LENGTH: 204
<212> TYPE: DNA
<213> ORGANISM: Homo sapiens

<400> SEQUENCE: 19

```
ggcgggaaca ggcggcgctg gacctgtacc cctacgacgc cgggacggac agcggcttca     60
ccttctcctc ccccaacttc gccaccatcc gcaggacga ggtgaccgag ataacgtcct    120
cctctcccag ccaccccggcc aactccttct actacccgcg gctgaaggcc ctgcctccca   180
tcgccagggt gacactggtg cggc                                           204
```

<210> SEQ ID NO 20
<211> LENGTH: 294
<212> TYPE: DNA
<213> ORGANISM: Homo sapiens
<220> FEATURE:
<221> NAME/KEY: misc_feature
<222> LOCATION: (287)..(287)
<223> OTHER INFORMATION: n=a, c, g or t

<400> SEQUENCE: 20

```
gagatttctc ttcaatggct tcctgtgagc tagagtttga aaatatctta aaatcttgag     60
ctagagatgg aagtagcttg gacgattttc attatcatgt aaatcgggtc actcaagggg   120
ccaaccacag ctgggagcca ctgctcaggg gaaggttcat atgggacttt ctactgccca   180
aggttctata caggatataa aggtgcctca cagtatagat ctggtagcaa agtaagaaga   240
aacaaacact gatctctttc tgccacccct ctgacccttt ggaactnctc tgac          294
```

<210> SEQ ID NO 21
<211> LENGTH: 22
<212> TYPE: DNA
<213> ORGANISM: Artificial Sequence
<220> FEATURE:
<223> OTHER INFORMATION: Synthetic

<400> SEQUENCE: 21

```
atcagaacaa agaggctgtg tc                                              22
```

<210> SEQ ID NO 22
<211> LENGTH: 21
<212> TYPE: DNA
<213> ORGANISM: Artificial Sequence
<220> FEATURE:
<223> OTHER INFORMATION: Synthetic

<400> SEQUENCE: 22

```
atctctaaag ccccaacctt c                                               21
```

<210> SEQ ID NO 23
<211> LENGTH: 19
<212> TYPE: DNA
<213> ORGANISM: Artificial Sequence
<220> FEATURE:

-continued

<223> OTHER INFORMATION: Synthetic

<400> SEQUENCE: 23
tgccgaagag gttcagtgc                                            19

<210> SEQ ID NO 24
<211> LENGTH: 22
<212> TYPE: DNA
<213> ORGANISM: Artificial Sequence
<220> FEATURE:
<223> OTHER INFORMATION: Synthetic

<400> SEQUENCE: 24
gccacagtgg tactgtccag at                                        22

<210> SEQ ID NO 25
<211> LENGTH: 21
<212> TYPE: DNA
<213> ORGANISM: Artificial Sequence
<220> FEATURE:
<223> OTHER INFORMATION: Synthetic

<400> SEQUENCE: 25
gctgcaagtt ctccacattg a                                         21

<210> SEQ ID NO 26
<211> LENGTH: 18
<212> TYPE: DNA
<213> ORGANISM: Artificial Sequence
<220> FEATURE:
<223> OTHER INFORMATION: Synthetic

<400> SEQUENCE: 26
cagccgcagg tgaaacac                                             18

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
tggctttgaa ctcagggtca                                           20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
cggatgcacc tcgtagacag                                           20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
cggcaacctg gtagtgagtg                                           20

<210> SEQ ID NO 30
<211> LENGTH: 22
<212> TYPE: DNA
<213> ORGANISM: Artificial Sequence
<220> FEATURE:
<223> OTHER INFORMATION: Synthetic

<400> SEQUENCE: 30
cgcagctcct tgtaaacttc ag                                              22

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
cgggaaccta ccagcctatg                                                 20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
caggcaacag ggagtcatgt                                                 20

<210> SEQ ID NO 33
<211> LENGTH: 18
<212> TYPE: DNA
<213> ORGANISM: Artificial Sequence
<220> FEATURE:
<223> OTHER INFORMATION: Synthetic

<400> SEQUENCE: 33
tgggcatctg ggtgtcaa                                                   18

<210> SEQ ID NO 34
<211> LENGTH: 19
<212> TYPE: DNA
<213> ORGANISM: Artificial Sequence
<220> FEATURE:
<223> OTHER INFORMATION: Synthetic

<400> SEQUENCE: 34
cggctgcgat gaggaagta                                                  19

<210> SEQ ID NO 35
<211> LENGTH: 22
<212> TYPE: DNA
<213> ORGANISM: Artificial Sequence
<220> FEATURE:
<223> OTHER INFORMATION: Synthetic

<400> SEQUENCE: 35
gcccatctcc tgcttcttta gt                                              22

<210> SEQ ID NO 36
<211> LENGTH: 21
<212> TYPE: DNA
<213> ORGANISM: Artificial Sequence
<220> FEATURE:
<223> OTHER INFORMATION: Synthetic

```
<400> SEQUENCE: 36
cgtggagatg gctctgatgt a                                                   21
```